US006919425B2

(12) United States Patent
Hong et al.

(10) Patent No.: US 6,919,425 B2
(45) Date of Patent: Jul. 19, 2005

(54) ISOLATION OF A CELL-SPECIFIC INTERNALIZING PEPTIDE THAT INFILTRATES TUMOR TISSUE FOR TARGETED DRUG DELIVERY

(75) Inventors: Frank D. Hong, Houston, TX (US); Gary Clayman, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 29 days.

(21) Appl. No.: 09/899,376

(22) Filed: Jul. 2, 2001

(65) Prior Publication Data

US 2002/0102265 A1 Aug. 1, 2002

Related U.S. Application Data

(60) Provisional application No. 60/215,491, filed on Jun. 30, 2000.

(51) Int. Cl.[7] .......................... A61K 38/00; A01N 37/18
(52) U.S. Cl. ............................................. 530/300; 514/2
(58) Field of Search ........................ 514/2, 12; 530/300

(56) References Cited

U.S. PATENT DOCUMENTS 5,087,616 A  * 2/1992 Myers et al.
6,303,576 B1 * 10/2001 Blaschuk et al.

FOREIGN PATENT DOCUMENTS

WO      WO 88/00837     * 2/1988

OTHER PUBLICATIONS

Prasad JA et al (Can. J. Physiol. Pharmocol. Feb. 1995;73(2):209–14).*
Bowie et al. Science, 247:1306–1310, 1990.*
Lazar et al. Molecular and Cellular Biology 8:1247–1252, 1988.*
Burgess et al., J of Cell Bio. 111:2129–2138, 1990.*
Arap et al., "Cancer treatment by targeted drug delivery to tumor vasculature in a mouse model," *Science*, 279:377–380, 1998.
Barry et al., "Toward cell–targeting gene therapy vectors: selection of cell–binding peptides from random peptide–presenting phage libraries," *Nature Med.*, 2:299–305, 1996.
Cherny et al., "Site–directed mutagenesis of the arginine—glycine–aspartic acid in vitronectin abolishes cell adhesion," *J. Biol. Chem.*, 268:9725–9729, 1993.

Clayman, "In vivo molecular therapy with p53 Adenovirus for Microscopic Residual Head and Neck Squamous Carcinoma," *Can. Res.*, 55:1–6, 1995.
D'Souza et al., "Arginyl–glycyl–aspartic acid (RGD): a cell adhesion motif," *Trends Biochem. Sci.*, 16(7):246–250, 1991.
Pasqalini et al., "Aminopeptidase N is a receptor for tumor–homing peptides and a target for inhibiting angiogenesis," *Cancer Res.*, 60(3):722–727, 2000.
Pasqualini and Ruoslahti, "Organ targeting in vivo using phage display peptide libraries," *Nature*, 380:364–366, 1996.
Wu et al., "Receptor–mediated in vitro gene transformation by a soluble DNA carrier system," *J. Biol. Chem.*, 262:4429–4432, 1987.
Behr et al., "Radiolabeled peptides for targeting Cholecystokinin–B/Gastrin receptor–expressing tumors," *J. Nucl. Med.*, 40:1029–1044, 1999.
Carpenter and Minchin, "Targeting of a cholecystokinin–DNA complex to pancreatic cells in vitro and in vivo," *Gene Therapy*, 5:848–854, 1998.
Hong and Clayman, "Isolation of a peptide for targeted drug delivery into human head and neck solid tumors," *Cancer Res.*, 60:6551–6556, 2000.
Koivunen et al., "Identification of receptor ligands with phage display peptide libraries," *J. Nucl. Med.*, 40:883–888, 1999.
Sauk et al., "Binding motifs of CBP2 a potential cell surface target for carcinoma cells," *J. Cell. Biochem.*, 78:251–263, 2000.
Schatzlein et al., "Targeting of tumor cells with peptides identified by phage display," *Proceedings of the American Association for cancer Research 91st Annual Meeting*, 41:103, Abstract # 655, 2000.
Wagner, "Receptor–mediated delivery of plasmid DNA," *Biogenic Amines*, 14(5):519–536, 1998.

* cited by examiner

*Primary Examiner*—G. Nickol
*Assistant Examiner*—C Yaen
(74) *Attorney, Agent, or Firm*—Fulbright & Jaworski

(57) ABSTRACT

The present invention provides a tumor-homing peptide that can target cancer and or tumor tissues. The peptide is uptaken by certain specific cancer cell types. The invention describes methods to achieve targeted delivery of anticancer drugs conjugated to this peptide for anticancer therapy. The invention also describes methods for using the peptide for the diagnosis and imaging of cancer and tumor tissues.

13 Claims, 4 Drawing Sheets

FIG. 1A-F

|  | Normal Human<br>Head and Neck Epithelium | Human Head and Neck<br>Invasive Squamous Cell Carcinoma |
|---|---|---|
| H&E | 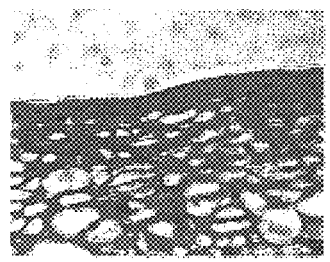 1 |  6 |
| Untreated | 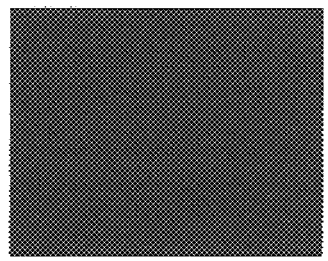 2 | 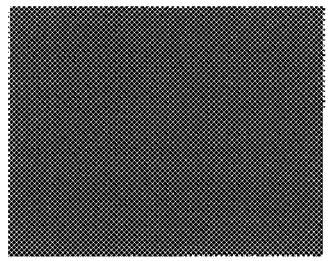 7 |
| FITC-HN-1 |  3 | 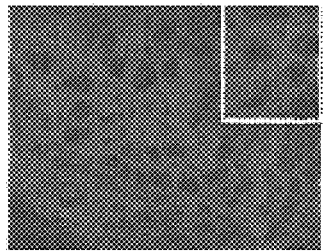 8 |
| Fluorescein | 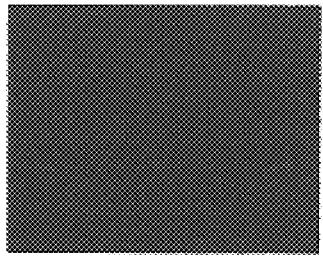 4 | 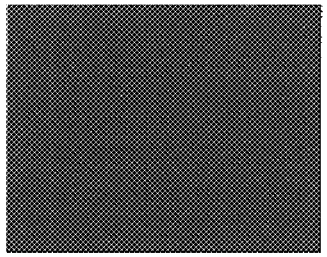 9 |
| FITC-HN-J | 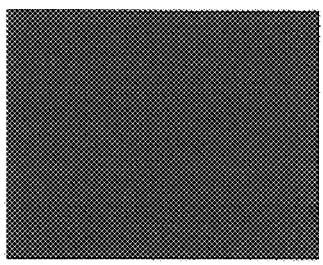 5 | 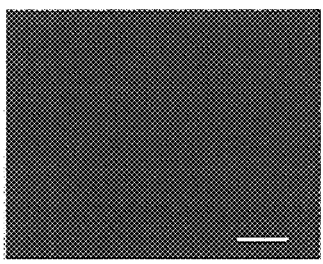 10 |
FIG. 2

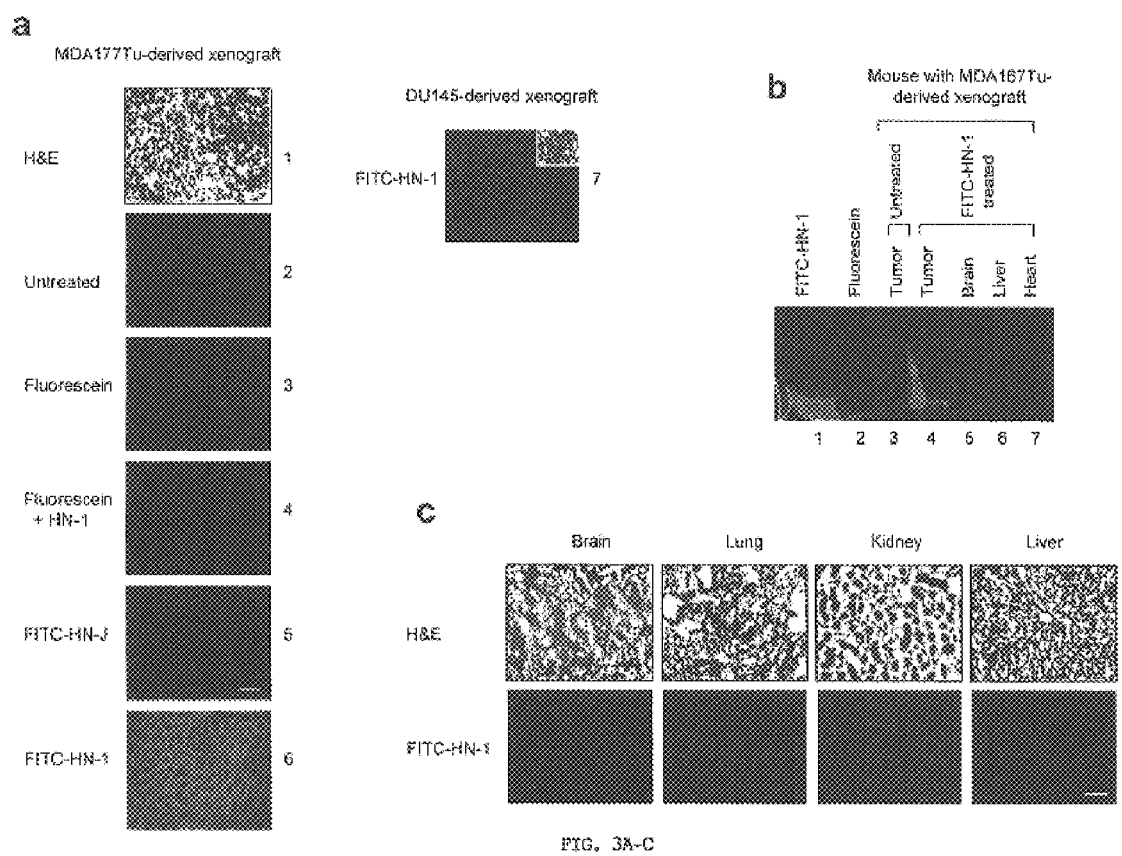
FIG. 3A-C

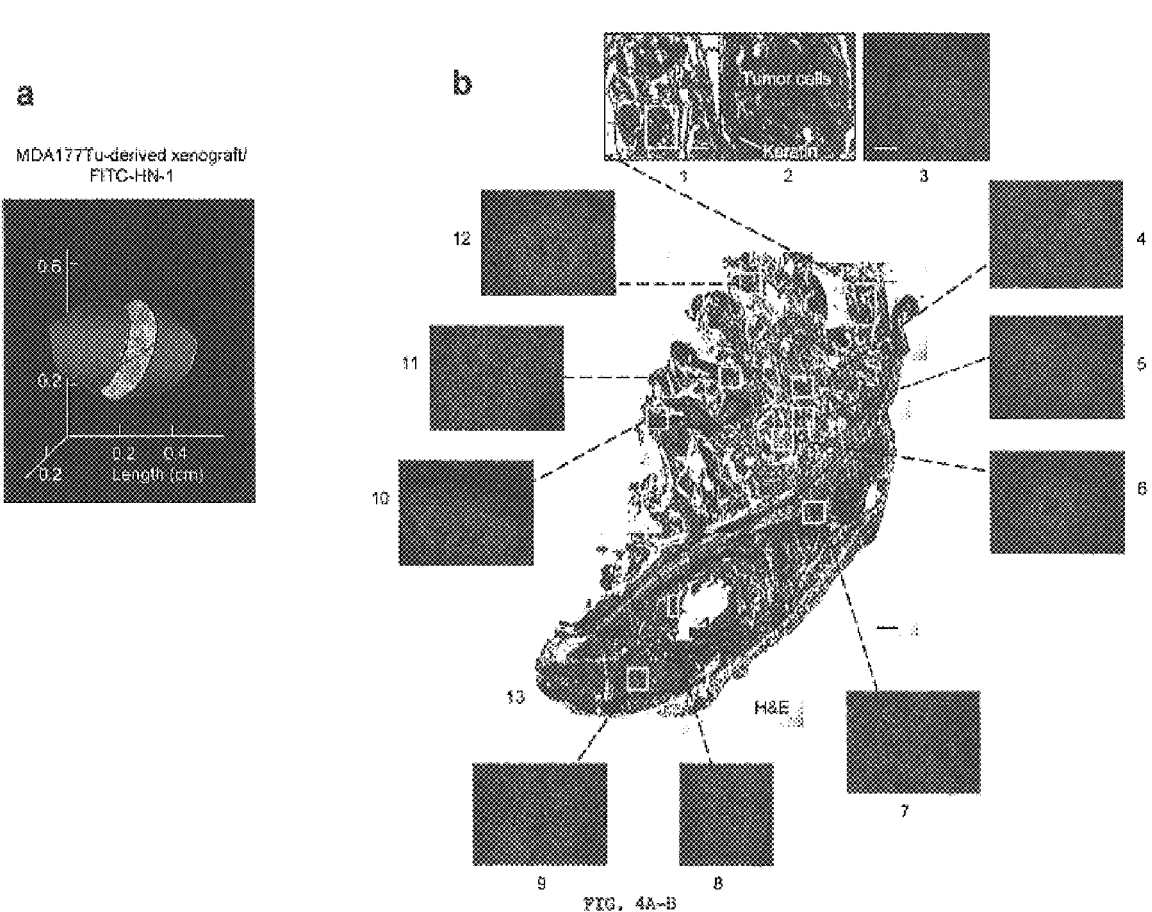
FIG. 4A-B

SEQUENCE LISTING

```
<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Thr Ser Pro Leu Asn Ile His Asn Gly Gln Lys Leu
 1               5                  10

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Gly Gly His
  1

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3
```

-continued

```
Gly Gly Gly Thr Ser Pro Leu Asn Ile His Asn Gly Gln Lys Leu Gly
 1               5                  10                  15

Gly Gly Ser

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Gly Ser Arg Arg Ala Ser Val Thr Ser Pro Leu Asn Ile His Asn Gly
 1               5                  10                  15

Gln Lys Leu

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Asn Gln His Ser Lys Asn Thr Leu Leu Ile Gly Pro
 1               5                  10
```

ISOLATION OF A CELL-SPECIFIC INTERNALIZING PEPTIDE THAT INFILTRATES TUMOR TISSUE FOR TARGETED DRUG DELIVERY

The application claims benefit of priority to U.S. Provisional Application U.S. Ser. No. 60/215,491 filed Jun. 30, 2000, the entire contents of which is hereby incorporated by reference.

The government owns rights in the present invention pursuant to grant number 5R29DE11689-04 from the National Institutes of Health and grant number 5P50DE11906-03 from the National Institutes of Dental and Craniofacial Research.

BACKGROUND OF THE INVENTION

1. Field of the Invention

The present invention relates generally to the fields of cellular and molecular biology. More particularly, it concerns the use of peptides that targets tumor tissue and describes methods to achieve targeted delivery of anticancer drugs using this peptide. The invention also contemplates methods for using the peptide for the diagnosis and imaging of cancer.

2. Description of Related Art

A. Cancers

Cancer is one of the leading causes of disease, being responsible for 526,000 deaths in the United States each year. In 1998, the American Cancer Society estimated that 60,000 Americans would be diagnosed with head and neck cancer. Head and neck cancer is the term given to a variety of malignant tumors that may occur in the head and neck region: the oral cavity (including the tissues of the lip or mouth such as the tongue, the gums, the lining of the cheeks and lips, the bottom of the mouth, the hard and soft palate and the retromolar trigone); the pharynx (including the hypopharynx, nasopharynx and oropharynx, also called the throat); paranasal sinuses (including the frontal sinuses above the nose, the maxillary sinuses in the upper part of either side of the upper jawbone, the ethmoid sinuses just behind either side of the upper nose, and the sphenoid sinus behind the ethmoid sinus in the center of the skull) and nasal cavity; the larynx (also called the voicebox); thyroid gland (including cancers of the thyroid which are papillary, follicular, medullary and anaplastic); parathyroid gland; salivary glands (including the major clusters of salivary glands found below the tongue, on the sides of the face just in front of the ears, and under the jawbone); lesions of the skin of the face and neck and the cervical lymph nodes; and metastatic squamous neck cancer with occult primary.

Although the percentage of oral and head and neck cancer patients in the United States is only about 5% of all cancers diagnosed, the importance of this disease is heightened by the fact that functional and aesthetic problems are commonly associated with this type of cancer and its treatment. Estimates indicate that there are more than 500,000 survivors of oral and head and neck cancer living in the United States today. Coping with this type of cancer can be extremely difficult. Not only can the disease be life-threatening, but many patients must also endure alterations in facial and neck appearance, as well as alterations in speech, sight, smell, chewing, swallowing and taste perception.

Head and neck cancers can arise from squamous cell carcinomas (SCC), which are the second most common form of skin cancer. They occur in men more often than women and originate primarily in skin exposed to the sun in a dose-dependent manner. SCCs are likely derived from keratinocytes located near the skin surface. Aneuploidy is common in this type of cancer, as is the presence of p53 mutations. SCC may occur anywhere on the skin, although it may arise on the mucosal membranes of the mouth, nose, lips, throat, eyelids, lining of the breathing tubes, anus, cervix, etc.

Breast cancer is the most common form of malignant disease among women in Western countries. In the United States it is the most common cause of death among women between 40 and 55 years of age. The American Cancer Society predicts there will be over 183,000 new cases of invasive breast cancer in the year 2000 and over 40,000 deaths. The incidence of breast cancer is increasing, especially in older women, but the cause of this increase is unknown. Several types of breast cancer include ductal carcinoma in situ (DCIS), infiltrating (invasive) ductal carcinoma (IDC), lobular carcinoma in situ (LCIS) and infiltrating (invasive) lobular carcinoma (ILC). Risk factors linked to the disease include smoking, age, family history, race (Caucasians are more susceptible) and menses history (early onset of menses and menopause after age 50 increases the risk).

An even more deadly form of cancer is cancer of the brain. Every year over 100,000 people are diagnosed with a primary or metastatic brain tumor, which is the second leading cause of cancer death in children under age 15 and in cancer deaths of young adults up to age 34. The nature of brain tumors located at the center for thought, emotion and physical function renders them difficult to treat, and the cure rate is significantly lower than for most other types of cancer. Brain tumors originate from one cell and travel to other brain cells instead of traveling to other organs, as occurs with other types of cancer. Brain tumors can originate in the brain itself (such as astrocytoma, glioblastoma, oligodendroglioma, and ependymoma), in its coverings (meningiomas, pituitary tumors, pineal tumors), in the nerves at the base of the brain (acoustic neuromas, schwannomas), or from outside the brain (metastatic brain tumors). The most common forms of brain tumor are the malignant astrocytoma and glioblastoma multiforme. Brain tumors do not metastasize, so treatment is usually limited to the brain. Furthermore, true tumor margins do not exist, so complete removal by local therapy, such as surgery, radiation, heat, cold, etc. is prohibitive. Treatments for the whole brain are preferred, since brain tumor cells travel around the brain. Furthermore, brain tumors can be polyclonal containing multiple tumors in one malignant mass.

Although a host of treatments for cancer, including various forms of chemotherapy, have been developed there is still the need for treatments that target only the tumor-specific tissue and spare other normal tissue. Such treatments are the cause of side effects associated with existing cancer therapies.

B. Tumor Therapy

The lack of tumor-specificity remains a major problem for chemotherapy since the deleterious side effects prevent the delivery of doses of drugs that are required to eliminate tumors (Hoekman, 1999; Lowenthal and Eaton, 1996; Wada, 1999; Shin et al., 1998). For solid tumors, which comprise >90% of all human cancers, antibodies recognizing tumor-specific antigens provide little utility for drug delivery because the immunoconjugates are unable to penetrate tumor tissue (Dvorak et al., 1991; Shockley et al., 1991; Pietersz and McKenzie, 1992), resulting in a high level of cytotoxic drugs in blood and dose-limiting myelotoxicity.

In the past, antibodies recognizing tumor-specific antigens have been used to deliver cytotoxic drugs to tumors. However, such immunoconjugates have shown limited effectiveness towards solid tumors due to their inability to penetrate into the interior of tumor tissue.

Although some studies have shown the isolation of peptides that specifically localize to certain cell/tissue types, their localization to cancer specific cells has not been demonstrated, thereby limiting utility in cancer therapy. For example, Barry et al. (1996), describe the isolation of several peptides that show a greater affinity towards mouse fibroblasts as compared to random peptides. The authors utilized a fd phage-based random peptide display library for screening, but the absence of a subtraction step to eliminate nonspecifically interacting phages resulted in the isolation of peptides that bound to multiple cell types, including hepatoma, myoblast, and mastocytoma cells in addition to fibroblasts. Thus, the peptides isolated by Barry and colleagues lack specificity towards any particular tissues, thereby limiting their utility.

In another related study, Pasqualini et al. (1996) performed an in vivo screening of a random peptide display library and isolated several peptides that localize to mouse brain and kidney through interaction with endothelial cells specific to those organs. Although binding of the peptides to those organs appeared specific, since their interaction was diminished in the presence of specific competitors, these peptides target normal organs of non-human origin and do not demonstrate any utility for a cancer treatment.

Finally, studies by Arap et al. (1998) described attempts to block tumor growth indirectly by inhibiting angiogenesis. Through in vivo screening of a random peptide display library, peptides that localized to endothelial cells associated with human breast carcinoma xenografts were isolated. Some of the peptides contained Arg-Gly-Asp sequence, a motif that binds to a subset of integrins. By conjugating the cytotoxic drug doxorubicin to the peptide, a selective destruction of blood vessels associated with tumors was observed. This, in turn, resulted in the necrosis of the tumor and an increase in the survivability of the tumor-bearing mice. Pasqualini et al. (2000) have determined this peptide interacts with aminopeptidase N, although this protein is produced in multiple tissues.

Furthermore, the mechanism through which the doxorubicin-peptide conjugate enters cells has not been delineated. For example, the study does not address if the peptide is internalized. Also, as the peptide targets endothelial cells rather than tumor cells directly, it is not a direct tumor-specific agent.

Thus, there is a need for development of agents that can direct chemotherapeutics to specific human tumor cells, as opposed to tumor-associated cells such as tumor-associated endothelial cells, thereby preventing the delivery of these drugs to normal non-cancerous cells, which in turn will prevent generalized cell damage and the associated side effects.

SUMMARY OF THE INVENTION

The present invention overcomes limitations in the art. The inventors describe herein the isolation of a peptide (HN-1) that is specifically internalized by the human head and neck squamous carcinoma cells. In certain embodiments of the invention, the HN-1 peptide also is specific to solid tumor tissue cells, such as breast cancer. The inventors also describe methods which allow specific delivery of anticancer drugs conjugated with HN-1 to tumor tissue. In addition, the inventors describe methods for imaging and diagnosis of cancer cells by conjugating HN-1 with detectable labels and delivering the conjugate to patients or by contacting the conjugate with tumor tissue in vitro. The inventors furthermore provide methods to isolate an internalizing peptide for a tumor. In addition, the inventors further describe methods to detect a cancer cell by isolation of an internalizing peptide and conjugation to a drug or gene therapy composition for administration to a patient.

The HN-1 peptide that the inventors have isolated differs from the peptide described in the Arap et al. (1998) study in that it is specific for the tumor cells rather than the tumor-associated endothelial cells. The present inventors envision conjugating any kind of anti-cancer drug to this peptide, to achieve a direct and specific killing of tumor cells. The natural ability of the peptide to enter tumor cells facilitates this process at the mechanistic level.

In an embodiment of the present invention there is a peptide that targets a tumor cell, wherein the peptide is internalized by the tumor cell. In a specific embodiment, the peptide comprises SEQ ID NO:1. In an additional embodiment the peptide consists of SEQ ID NO:1. In another embodiment of the present invention there is a DNA segment encoding SEQ ID NO:1. In a specific embodiment the DNA segment comprises a nucleic acid that encodes SEQ ID NO:1. In an additional specific embodiment the DNA segment is further defined as a recombinant vector.

In another embodiment of the present invention there is provided a composition comprising a drug; and a peptide that targets a tumor cell, wherein the peptide is internalized by said tumor cell. In a specific embodiment the peptide comprises SEQ ID NO:1. In a specific embodiment the peptide consists of SEQ ID NO:1. In a further specific embodiment the drug is a chemotherapeutic agent. In another specific embodiment the drug is a cytotoxic agent. In an additional specific embodiment the drug is an apoptotic agent. In a further specific embodiment the drug is a DNA-damaging agent. In another specific embodiment the drug is Taxol. In an additional specific embodiment the drug is cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin or methotrexate.

In accordance with an object of the present invention, there is provided a method for killing a tumor cell comprising contacting the tumor cell with a pharmaceutically acceptable composition comprising a drug; and a peptide that targets the tumor cell, wherein the peptide is internalized by the tumor cell. In a specific embodiment the peptide comprises SEQ ID NO:1. In another specific embodiment the drug is conjugated to the peptide. In a further specific embodiment the tumor cell is selected from the group consisting of squamous cell carcinomas, head and neck cancers, breast cancers, glioblastomas and astrocytomas. In a specific embodiment the tumor cell is a human head and neck cancer cell. In a specific embodiment the human head and neck cancer cell is an oral cavity cell, a pharynx cell, a throat cell, a paranasal sinus cell, a nasal cavity cell, a larynx cell, a thyroid cell, a parathyroid cell, a salivary gland cell, a skin cell of the face, a skin cell of the neck or a cervical lymph node cell. In another specific embodiment the tumor cell is a solid tumor cell. In a further specific embodiment the solid tumor cell comprises a breast cancer cell. In a specific embodiment the contacting is by intravenous administration, intratumoral administration, subcutaneous administration, intraperitoneal administration or topical administration. In an additional specific embodiment the contacting is by local, regional or systemic administration. In another specific embodiment the tumor cell is in a patient.

In accordance with another aspect of the present invention there is provided a method for detecting cancer comprising obtaining a peptide comprising SEQ ID NO:1, wherein the peptide targets a tumor cell; conjugating a detectable label to the peptide; administering the conjugated peptide and label to a patient; and detecting binding of the conjugate to tumor cells by suitable detection means. In a specific embodiment the binding further comprises uptake by said tumor cells. In another specific embodiment the label is a radionucleotide, a fluor or a spin label. In an additional specific embodiment the administering is by intravenous injection, intratumoral injection, subcutaneous injection, intraperitoneal injection or topical administration. In a specific embodiment the administering is by local, regional or systemic administering. In an additional embodiment the detection is by magnetic resonance imaging, x-ray imaging or computerized emission tomography.

In accordance with other objects of the present invention there is provided a method for detecting a tumor in vitro comprising obtaining a peptide comprising SEQ ID NO:1, wherein said peptide targets the tumor; conjugating a detectable label to the peptide; contacting the conjugated peptide and label to the tumor-containing sample; and detecting binding of the conjugate to the tumor by suitable detection means. In a specific embodiment the binding further comprises uptake by cells of the tumor. In a specific embodiment the label is a radionucleotide, a fluor or a spin label. In another embodiment the detection is by nuclear magnetic resonance imaging, x-ray imaging, computerized emission tomography or positron emission tomography.

In accordance with another object of the present invention there is provided a tumor-detection kit comprising, in suitable container means, a pharmaceutical composition of a peptide comprising SEQ ID NO:1. In a further specific embodiment there is a tumor-detection kit comprising, in suitable container means, a pharmaceutical composition of a peptide comprising SEQ ID NO:1 bound to a detectable label, wherein said peptide targets a tumor cell. In another specific embodiment there is a tumor-detection kit comprising, in suitable container means a pharmaceutical composition of a peptide comprising SEQ ID NO:1 bound to a detectable label, wherein the peptide targets a tumor cell; and a suitable means for detection. In a specific embodiment the detectable label is detectable by non-invasive means. In another specific embodiment the detectable label is a spin-labeled molecule. In an additional specific embodiment the detectable label is a radioactive isotope. In an additional specific embodiment the detection means is by nuclear magnetic resonance imaging, x-ray imaging, computerized emission tomography, or positron emission tomography.

In accordance with another aspect of the present invention there is provided a tumor-imaging kit comprising, in a suitable container means, an effective amount of a pharmaceutically acceptable formulation comprising a peptide comprising SEQ ID NO:1, wherein said peptide targets a tumor cell. In a specific embodiment the tumor-imaging kit comprises, in a suitable container means, an effective amount of a pharmaceutically acceptable formulation comprising a peptide comprising SEQ ID NO:1, wherein said peptide targets a tumor cell and wherein said peptide is bound to a detectable label. In a further specific embodiment the tumor-imaging kit comprises, in suitable container means, an effective amount of a pharmaceutically acceptable formulation comprising a peptide comprising SEQ ID NO:1, wherein the peptide targets a tumor cell and wherein the peptide is further bound to a detectable label; and a suitable means for detecting said detectable label. In a specific embodiment the detectable label is imaged by non-invasive means. In another specific embodiment the detectable label is a spin-labeled molecule. In a further specific embodiment the detectable label is a radioactive isotope. In a specific embodiment the detection means is by nuclear magnetic resonance imaging, x-ray imaging, computerized emission tomography or positron emission tomography.

In accordance with an object of the present invention there is a method for killing a tumor cell comprising administering to a patient radiotherapy; and a pharmaceutically acceptable composition comprising an anti-tumor compound conjugated to a peptide that targets said tumor cell, wherein said peptide is internalized by said tumor cell. In a specific embodiment the peptide comprises SEQ ID NO:1. In an additional embodiment the radiotherapy is administered whole body, local, or regional. In an additional specific embodiment the radiotherapy is radioisotopic irradiation, γ-irradiation, X-ray irradiation, UV-irradiation, microwave irradiation or electronic irradiation. In a specific embodiment the patient is administered about 40 to about 100 Gy radiation. In another specific embodiment the patient is administered about 55 to about 65 Gy radiation. In an additional specific embodiment the patient is administered 62 Gy radiation. In a specific embodiment the tumor cell is selected from the group consisting of squamous cell carcinoma, head and neck cancer and breast cancer.

In accordance with an object of the present invention there is provided a method for killing a tumor cell comprising administering to a patient chemotherapy; and a pharmaceutically acceptable composition comprising an anti-tumor compound conjugated to a peptide that targets said tumor cell, wherein said peptide is internalized by said tumor cell.

In accordance with an object of the present invention there is provided a method for killing a tumor cell comprising administering to a patient chemotherapy; and a pharmaceutically acceptable composition comprising a liposome linked to a peptide that targets said tumor cell, wherein said liposome comprises an anti-tumor compound, and wherein said peptide is internalized by said tumor cell.

In accordance with another object of the present invention there is provided a method for killing a tumor cell comprising administering to a patient surgery; and a pharmaceutically acceptable composition comprising an anti-tumor compound conjugated to a peptide that targets said tumor cell, wherein said peptide is internalized by said tumor cell.

In accordance with another object of the present invention there is a method for killing a tumor cell comprising administering to a patient gene therapy; and a pharmaceutically acceptable composition comprising an anti-tumor compound conjugated to a peptide that targets said tumor cell, wherein said peptide is internalized by said tumor cell. In a specific embodiment the gene therapy is directed to a nucleic acid sequence selected from the group consisting of ras; myc, raf, erb, src, fms, jun, trk, ret, gsp, hst, bcl abl, Rb, CFTR, p16, p21, p27, p53, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF G-CSF and thymidine kinase.

In accordance with an additional object of the present invention there is a tumor-treating kit in suitable container means comprising a therapeutically effective amount of a pharmaceutically acceptable formulation comprising a peptide comprising SEQ ID NO:1, wherein said peptide targets a tumor cell. In a specific embodiment the tumor-treating kit in suitable container means comprises a therapeutically effective amount of a pharmaceutically acceptable formulation comprising a peptide comprising SEQ ID NO:1, wherein said peptide targets a tumor cell and an anti-tumor compound. In a specific embodiment the anti-tumor compound is Taxol. In another specific embodiment the anti-tumor compound is selected from the group consisting of cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin and methotrexate.

In accordance with another object of the present invention there is a composition comprising a peptide comprising SEQ ID NO:1, wherein said peptide targets a tumor cell; and a vector comprising a composition for gene therapy. In a specific embodiment the vector is selected from the group consisting of a protein, a peptide, a liposome, a lipid, a nucleic acid and a combination thereof. In a specific embodiment the composition for gene therapy comprises a nucleic acid. In an additional specific embodiment the composition for gene therapy comprises a p53 nucleic acid. In a further specific embodiment the composition for gene therapy comprises a nucleic acid selected from the group consisting of ras, myc, raf, erb, src, fms, jun, trk, ret, gsp, hst, bcl abl, Rb, CFTR, p16, p21, p27, p53, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF G-CSF G-CSF and thymidine kinase.

In accordance with another object of the present invention there is provided a method to treat an organism for cancer comprising contacting said organism with a therapeutically effective amount of a pharmaceutically acceptable composition comprising a peptide comprising SEQ ID NO:1, wherein said peptide targets a tumor cell; and an antitumor compound. In a specific embodiment the antitumor compound is conjugated to said peptide. In another specific embodiment the antitumor compound is Taxol. In a further specific embodiment the antitumor compound is selected from the group consisting of cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin and methotrexate. In a specific embodiment the cancer is selected from the group consisting of squamous cell carcinoma, head and neck cancer and breast cancer.

In accordance with an additional object of the present invention there is provided a method for the isolation of an internalizing peptide comprising the steps of obtaining a peptide library; individually contacting peptides of said library with members of a cell population; and assaying for endocytosis of said peptides by said members of said cell population. In a specific embodiment the peptide library is a random peptide-display library. In a specific embodiment the peptide library is a M13 single-stranded bacteriophage-based random peptide-display library. In a specific embodiment the cell is a cancer cell.

In another embodiment of the present invention there is a method for detecting cancer comprising the steps of obtaining an internalizing peptide; conjugating a detectable label to said peptide; administering the conjugated peptide and label to an organism; and detecting binding of said conjugate to cancer cells by suitable detection means.

In an additional embodiment of the present invention there is a method for detecting cancer comprising the steps of obtaining a peptide library; individually contacting peptides of said library with members of a cell population; assaying for endocytosis of said peptides by said members of said cell population to identify an internalizing peptide; conjugating a detectable label to said peptide; administering the conjugated peptide and label to an organism; and detecting binding of said conjugate to a cell by suitable detection means.

The inventors envision that this will allow one to provide the necessary dose of a drug to destroy tumors without being restricted by the occurrence of harmful side effects to other cells. The potential for HN-1 as a shuttle for drug delivery is further strengthened by the fact that it is nontoxic, nonimmunogenic, stable in vivo (shown by detecting intact peptide in blood 24 h after injection), protects its cargo during transit, and accumulates sufficiently in a tumor or tumors within 48 hours.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 1A through 1C and 1F show fluorescence microscopy, wherein Nomarsky optics of the corresponding views are shown in 1A, 1B and 1F. FIG. 1A demonstrates MDA177Tu cells were incubated with the indicated agent. In FIG. 1B through 1F peptide incubation was performed as in FIG. 1A. FIG. 1B shows indicated cells which were incubated with FITC-HN-1. FIG. 1C demonstrates MDA177Tu cells which were incubated with the indicated agent. FIG. 1D illustrates a protease protection assay. FITC-HN-1 incubated MDA177Tu cells (lanes 4–7) were treated as indicated, electrophoresed, and viewed as described in Examples. FIG. 1E illustrates subcellular fractionation. MDA177Tu cells incubated with FITC-HN-1 were separated into nuclear (lane 2), cytoplasmic (lane 3) and cell membrane (lane 4) fractions, electrophoresed, and viewed. Equivalent amounts of each fraction were loaded. FIG. 1F shows a competition assay. MDA177Tu cells were incubated with FITC-HN-1 in the presence of excess unlabeled specific competitor (SP) or a nonspecific competitor (NSP). (Bar size, 58 $\mu$m for (FIG. 1A); 38 $\mu$m for (FIG. 1B); 14 $\mu$m for (FIG. 1C); 29 $\mu$m for (FIG. 1F))

FIG. 2 demonstrates HN-1 binds to primary HNSCC. Histological sections (containing tumor and the corresponding normal tissue) of a human head and neck squamous cell cancer biopsy sample were incubated with the indicated agent and viewed by fluorescence microscopy, as described in Examples. The data shown represent the results of three independent experiments. The inset indicates amplified views of tumor cells. (Bar=21 $\mu$m)

FIGS. 3A through 3C illustrate that HN-1 localizes to HNSCC cell-derived xenograft in vivo. FIG. 3A Cryostat section of MDA177Tu- or DU145-derived xenograft resected from a mouse treated with the indicated agent. Hemotoxylin and eosin (H&E) staining of a representative tumor is shown. FIG. 3B shows electrophoretic analysis. Electrophoretic analysis. Tumor or normal tissue extract from a mouse harboring MDA167Tu-derived xenograft that was treated as indicated. FIG. 3C demonstrates fluorescence microscopy of various normal tissues from a mouse with MDA177Tu-derived xenograft that was treated with FITC-HN-1. H&E staining of the corresponding views are shown. In all experiments, animals were treated with the indicated agent for 48 h. (Bar (um)=92(a), 48(c))

FIGS. 4A through 4B demonstrate HN-1 infiltrates tumor tissue in vivo. Histological sections were prepared from the middle part of a MDA177Tu-derived HNSCC xenograft resected from a mouse that had been treated with FITC-HN-1 as described in FIG. 3A. FIG. 4A shows a schematic representation of the region shown in FIG. 4B. The tumor shown is identical to that shown in FIG. 3A (panel 6). FIG. 4B demonstrates H&E staining (panels 1, 2, 13 (montage)). Fluorescence micrographs are shown in panels 3–12. Panel 2 is an amplified view of boxed region in Panel 1. Panel 3 is a fluorescence micrograph of adjacent section corresponding to panel 2. (Bar (um)=78 (panel 1); 48 (panel 2–12 ); 240 (panel 13)).

DESCRIPTION OF ILLUSTRATIVE EMBODIMENTS

Figure 1:
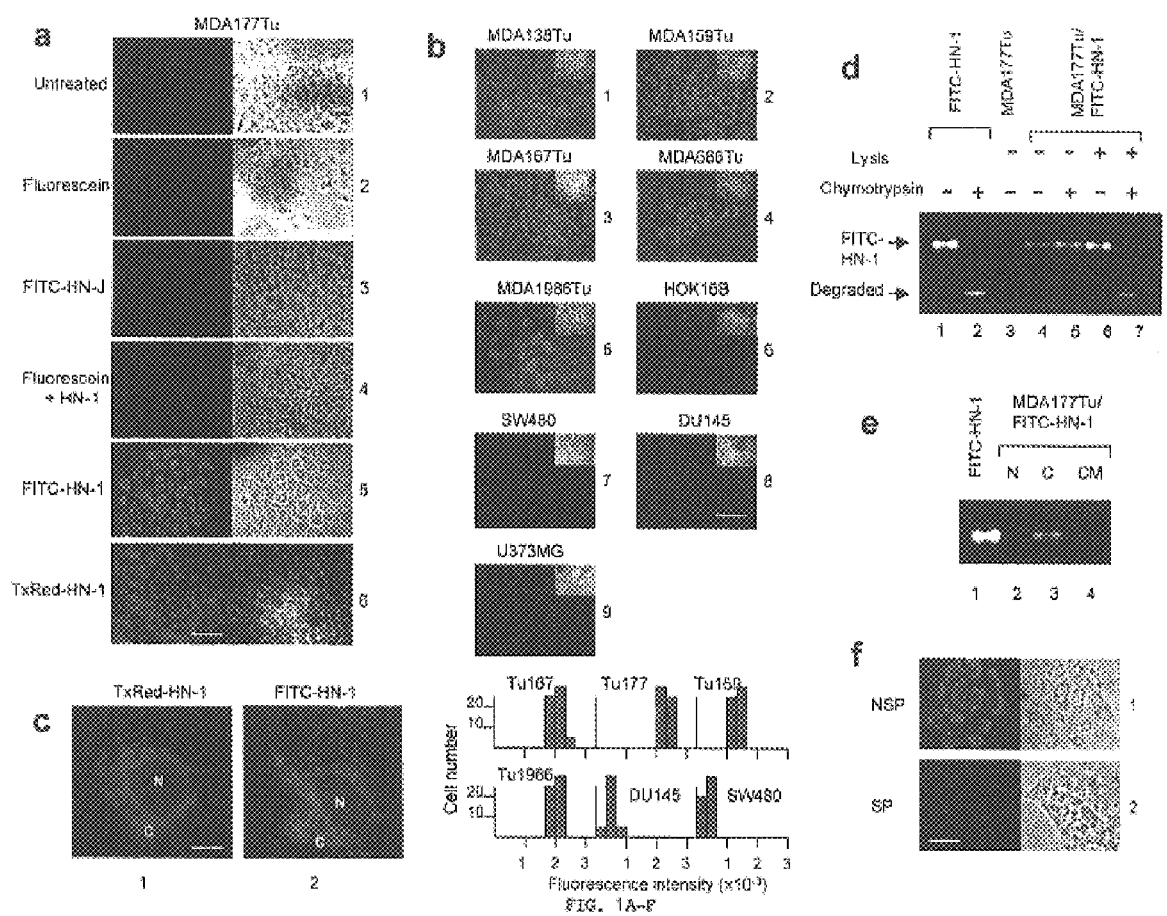
FIGS. 1A through 1F show internalization of HN-1.

The present invention is directed toward utilization of an amino acid SEQ ID NO:1 conjugated to a compound for delivery of the conjugated complex to a tumor. The ability of this peptide permits targeting anti-cancer drugs to tumors, such as head and neck squamous carcinomas and breast cancer. In other specific embodiments the peptide facilitates imaging and diagnosis of cancer cells through conjugation to detectable labels and subsequent delivery to tumor tissue in a patient.

The following definitions are provided:

The term "apoptotic agent" as used herein is defined as a drug, toxin, compound, composition or biological entity which bestows apoptosis, or programmed cell death, onto a cell. In a specific embodiment the cell is a tumor cell. In another embodiment the tumor cell is a head and neck cancer cell, a squamous cell carcinoma, a brain tumor cell or a breast cancer cell.

The term "cancer" as used herein is defined as a tissue of uncontrolled growth or proliferation of cells, such as a tumor. In a specific embodiment the tumor leads to local invasion and metastasis.

The term "chemotherapeutic agent" as used herein is defined as a drug, toxin, compound, composition or biological entity which is used as treatment for cancer.

The term "conjugate" as used herein is defined as the tethering or binding of a HN-1 peptide with another entity, such as a drug, composition, compound, or detectable label. The conjugation is executed in a specific embodiment by a chemical reaction associated with, for example, a thiol group or amine group of the HN-1 peptide and an activated group on the corresponding drug. A skilled artisan is aware that the chemical reaction would depend on what functional groups were present on HN-1 or its derivatives and what corresponding functional groups were present on the drug.

The term "cytotoxic agent" as used herein is defined as a drug, toxin, compound, composition or biological entity which is used to kill a cell. In a specific embodiment the cell is a tumor cell. In another embodiment the tumor cell is a head and neck cancer cell, a squamous cell carcinoma, or a breast cancer cell.

The term "delivery" as used herein is defined as the molecular conveyance provided by a peptide or fragment of HN-1 for a compound to which it is bound or conjugated to a tumor or tumor cell. The targeting may be directly to the tumor or tumor cell upon administration or may be by indirect means or mechanisms. It is within the scope of the term to permit the conjugate comprising the HN-1/compound to follow an indirect path for eventually targeting the tumor or tumor cell, including binding for non-therapeutic purposes to other biological entities. The term "delivery" as used herein may be used interchangeably with the term "targeting."

The term "DNA-damaging agent" as used herein is a drug, toxin, compound, composition or biological entity which damages nucleic acid. The damage may be of any kind to the nucleic acid, for example, to break one or both strands of a DNA double helix molecule or to cause mutation of one or more nucleotides.

The term "drug" as used herein is defined as a medicament or medicine which is used for the therapeutic treatment of a medical condition or disease. The drug may be used in combination with another drug or type of therapy and in a preferred embodiment is effective for the treatment of cancer.

The term "head and neck cancer" as used herein is defined as any of a variety of malignant tumors that may occur in the head and neck region: the oral cavity (including the tissues of the lip or mouth such as the tongue, the gums, the lining of the cheeks and lips, the bottom of the mouth, the hard and soft palate and the retromolar trigone); the pharynx (including the hypopharynx, nasopharynx and oropharynx) (also called the throat); paranasal sinuses (including the frontal sinuses above the nose, the maxillary sinuses in the upper part of either side of the upper jawbone, the ethmoid sinuses just behind either side of the upper nose, and the sphenoid sinus behind the ethmoid sinus in the center of the skull) and nasal cavity; the larynx (or voicebox); thyroid gland (including cancers of the thyroid which are papillary, follicular, medullary and anaplastic); parathyroid gland; salivary glands (including the major clusters of salivary glands found below the tongue, on the sides of the face just in front of the ears, and under the jawbone); lesions of the skin of the face and neck and the cervical lymph nodes; and metastatic squamous neck cancer with occult primary.

The term "internalizing" as used herein is defined as the uptake of at least part of the HN-1 peptide or another peptide isolated by similar means as described herein into a tumor or into a tumor cell. Internalizing into a tumor cell means a part or all of a peptide such as HN-1 is taken into the cell, which includes retention of part or all of the peptide in or into the membrane of the cell. The internalizing may be transient or permanent.

The term "label" as used herein is defined as an entity bound or conjugated, either directly or indirectly, to a HN-1 peptide which allows for detection of the peptide. The label may be a fluorophore, a chromophore, a radioactive label or any means to facilitate detection of the peptide.

The term "oral cancer" as used herein is defined as cancer of the oral cavity.

The term "oral cavity" as used herein is defined as any of the tissues of the lip or mouth such as the tongue, the gums, the lining of the cheeks and lips, the bottom of the mouth, the hard and soft palate and the retromolar trigone (the region behind the wisdom teeth).

The term "peptide" as used herein is defined as a chain of up to about 50 amino acids.

The term "pharmaceutically or pharmacologically acceptable" as used herein refers to molecular entities and compositions that do not produce adverse, allergic, or other untoward reactions when administered to an animal or a human.

The term "pharmaceutically acceptable carrier" as used herein includes any and all solvents, dispersion media, coatings, antibacterial and antifungal agents, isotonic and absorption delaying agents and the like.

The term "recombinant vector" as used herein is defined as a means to transfer a sequence comprising a nucleic acid encoding HN-1 or another internalizing peptide into a cell. In specific embodiments a vector is a nucleic acid, an amino acid, a protein, a peptide, a lipid, a liposome, a carbohydrate, a sugar, a fatty acid, or a combination thereof.

The term "specific," as used herein, is defined in one embodiment as delivery or targeting by an HN-1 peptide or another internalizing peptide conjugated to an antitumor compound to cancerous tissue. In a another embodiment, the term specific means an HN-1 peptide or another internalizing peptide delivers or targets an antitumor compound preferentially to cancerous tissue. In a yet another embodiment, the term refers to delivery or targeting of cancerous tissue for an antitumor compound in which a conjugate comprising an HN-1 peptide or another internalizing peptide binds nothing else but the cancerous tissue. In one aspect of these embodiments, the conjugate described herein may contact other biological entities during the process or journey of delivery of the conjugate to a tumor.

The term "targets" as used herein is defined as the molecular direction provided by a HN-1 peptide or fragment thereof for a compound to which it is bound or conjugated to a tumor or tumor cell. The targeting may be directly to the tumor or tumor cell upon administration or may be by indirect means or mechanisms. It is within the scope of the term to permit the conjugate comprising the HN-1/ compound to follow an indirect path for eventually targeting the tumor or tumor cell, including binding for non-therapeutic purposes to other biological entities.

The term "to treat" as used herein is defined as the practice of applying a treatment for a medical condition or disease. The treatment need not provide a complete cure and is considered effective if at least one symptom is improved upon or eradicated. Furthermore, the treatment need not provide a permanent improvement of the disease state or medical condition, although this is preferable.

The term "tumor cell" as used herein is defined as a cell of a malignant mass, such as a tumor or cancer. The cell may be located within the tumor, on the surface of the tumor, or it may be associated with the tumor.

The present invention describes the identification of a peptide (HN-1), bearing SEQ ID NO:1, that is specifically internalized by the human head and neck squamous carcinoma cells or certain other solid tumor tissue cells, such as breast cancer cells. The inventors envision the use of the HN-1 peptide to achieve tumor-tissue specific delivery of diagnostics and anticancer drugs to cancerous tissue. Thus, in certain embodiments of the invention, the inventors describe methods developed to conjugate anticancer drugs with the HN-1 peptide and methods which allow delivery of the peptide-conjugated drugs to specific tumor tissues. In other embodiments, the inventors describe methods that can be used to achieve selective killing of cancer and/or tumor cells in cancer patients by contacting the tumor with pharmaceutically acceptable compositions of the HN-1 peptide and a drug conjugate. In yet other embodiments, methods for imaging cancers using HN-1 peptide conjugated labels are described for both in vitro and in vivo applications. Thus, the development of cancer therapeutic and diagnostic kits are described.

In the past, antibodies recognizing tumor-specific antigens have been used to deliver cytotoxic drugs to tumors. However, these immunoconjugates have shown limited effectiveness towards solid tumors due to their inability to penetrate tumor tissue. In contrast, the 12-mer peptide (HN-1) that the inventors have isolated is $1/100^{th}$ in mass when compared to typical antibodies and is capable of penetrating tumors such as human head and neck squamous cell cancer (HNSCC) xenograft, formed in nude mice. Thus, by conjugating the HN-1 peptide to drugs, the inventors have developed a tumor-specific delivery system for drugs in systemic deposits of cancer cells.

The inventors screened a random-peptide display library (described in the Examples), containing >$10^9$ random peptides and isolated the HN-1 peptide that is specific to the human head and neck squamous cell cancers (HNSCC). Through fluorescence microscopy, the internalization of fluorescent dye-conjugated HN-1 peptide into HNSCC cells was documented in vitro. The peptide localized in cytoplasm after entry. This was further confirmed by electrophoretic analysis of subcellular fractions of peptide-incubated cell lysate. A limited uptake of the HN-1 peptide occurred in human oral keratinocytes (HPV immortalized). Taken together, this demonstrates that the peptide is specific for certain cancers. Furthermore, the HN-1 peptide bound preferentially to HNSCC cells as compared to normal cells at the primary cell level. In vivo, intravenously injected HN-1 peptide localized to HNSCC xenograft formed in nude mice. The peptide accumulated in the cytoplasm throughout the tumor, demonstrating its ability to penetrate the interior of the tumor mass.

To mimic drug delivery, HN-1 was conjugated to fluorescein, a complex organic molecule with ~44% molecular mass of Taxol. After intravenous administration, FITC-conjugated HN-1 localized to human head and neck cancer cell-derived xenografts. The peptide was found throughout the tumor, demonstrating its capacity to infiltrate tumor tissue carrying a conjugated compound.

In a preferred embodiment of the present invention a HN-1 peptide is conjugated or bound to an antitumor drug such as Taxol. The antitumor drug is generally hydrophobic enough to permit diffusion across tumor cell membrane, although it is within the scope of the invention for the HN-1 peptide to target the drug to a tumor cell and allow translocation or internalization of the anti-tumor drug by other means.

Although the art describes certain peptides that have previously been used to deliver cytotoxic drugs into solid tumors, none of the peptides are tumor-specific. One type includes high molecular weight cationic polymers such as poly-L-lysine (Wu et al., 1987) that are selectively retained by the tumors due to the leaky tumor vasculature and the other type includes peptides that bind selectively to tumor vasculature, allowing the destruction of angiogenic endothelial vessels necessary for tumor growth. However, as tumors smaller than 1 mm in diameter can persist through nutrients obtained from adjacent normal blood vessels (Folkman, 1990), the task of eliminating these smaller tumors still remains. The current invention resolves these problems by providing a tumor specific peptide, HN-1, that is capable of penetrating and/or being uptaken by solid tumors. The invention is directed to the coupling of an HN-1 peptide to anticancer drugs, which when administered to an animal, provide tumor-specific targeting of the anticancer drug and therefore provide an effective anticancer therapy.

The inventors envision that this will allow one to provide the necessary dose of a drug to destroy tumors without being restricted by the occurrence of harmful side effects to other cells. The potential for HN-1 as a shuttle for drug delivery is further strengthened by the fact that it is nontoxic, nonimmunogenic, stable in vivo (shown by detecting intact peptide in blood 24 h after injection), protects its cargo during transit, and accumulates sufficiently in a tumor within 48 hours.

1. Peptides

A. HN1

The inventors contemplate the use of HN-1 for the diagnosis and treatment of head and neck cancers. It also is contemplated that HN-1 may be used for the treatment of other solid tumors such as breast cancers and brain tumors.

Thus, in one embodiment, the inventors conjugate Taxol, the most potent chemotherapeutic for treating HNSCC (Shin et al., 1998) and breast cancers, to HN-1. In other embodiments, HN-1 is conjugated to other chemotherapeutic agents.

In other embodiments there are several uses of HN-1 which include but are not limited to use in tumor imaging, tumor diagnosis, and providing tumor-specificity to gene transfer approaches (Clayman et al, 1995).

In one embodiment of the present invention there is a peptide that targets a tumor cell, and in a specific embodiment is internalized by the tumor cell. An object of the present invention is a peptide comprising or consisting of SEQ ID NO:1. In a preferred embodiment of the present invention there is internalization of the peptide, although it is within the scope of the present invention to utilize a HN-1 peptide or another internalizing peptide to target through direct or indirect means or mechanisms an anti-cancer drug to a tumor.

In an object of the present invention there is a composition comprising a drug and a HN-1 peptide which targets a tumor cell and in a specific embodiment becomes internalized by said tumor cell. In specific embodiments the drug is a chemotherapeutic agent, a cytotoxic agent, an apoptotic agent, a DNA-damaging agent, or Taxol. In a specific embodiment the drug is cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin or methotrexate.

B. Variants of HN-1

Amino acid sequence variants of HN-1 also are encompassed by the present invention. Amino acid sequence variants of the polypeptide can be substitutional variants or insertional variants.

Insertional mutants typically involve the addition of material at a non-terminal point in the peptide. This may include the insertion of a few residues; an immunoreactive epitope; or simply a single residue. The added material may be modified, such as by methylation, acetylation, and the like. Alternatively, additional residues may be added to the N-terminal or C-terminal ends of the peptide.

Substitutional variants typically contain the exchange of one amino acid for another at one or more sites within the peptide, and may be designed to modulate one or more properties of the peptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a peptide to create an equivalent, or even an improved, second-generation molecule. For example, certain amino acids may be substituted for other amino acids in a peptide/protein structure without appreciable loss of interactive binding capacity with structures such as, for example, binding sites on substrate molecules or antigen-binding regions of antibodies. Since it is the interactive capacity and nature of a peptide/protein that defines that peptide/protein's biological functional activity, certain amino acid substitutions can be made in a peptide/protein sequence, and its underlying DNA coding sequence, and nevertheless obtain a protein with like properties. It is thus contemplated that various changes may be made in the DNA sequences of genes without appreciable loss of their biological utility or activity, as discussed below. Furthermore, the amino acids of the present invention may contain alterations such as methylation, acetylation, myristilation, and the like.

In making such changes, the hydropathic index of amino acids may be considered. The importance of the hydropathic amino acid index in conferring interactive biologic function on a peptide/protein is generally understood in the art (Kyte and Doolittle, 1982). It is accepted that the relative hydropathic character of the amino acid contributes to the secondary structure of the resultant peptide/protein, which in turn defines the interaction of the peptide/protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide/protein with similar biological activity, i.e., still obtain a biological functionally equivalent peptide/protein. In making such changes, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. However, alterations to the amino acids of the present invention may be other than conservative and still within the scope of the present invention so long as the peptides still retain the function to target tumor cells.

Another embodiment for the preparation of peptides according to the invention is the use of peptide mimetics. Mimetics are peptide-containing molecules that mimic elements of protein secondary structure. See, for example, Johnson et al., 1993. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of HN-1, but with altered and even improved characteristics. For example, substitution of amino acids to generate motifs that have stronger binding to tumor cells; or that can be specifically tailor-made to bind different types of tumor cells can allow the generation of more HN-1 related peptides, each different for a different tumor-type.

In an embodiment of the present invention there are additional means associated with a peptide comprising HN-1 or a fragment or derivative thereof which facilitate transduction or internalization of the peptide-antitumor composition conjugate to a tumor cell. In a specific embodiment, a protein transduction domain is also bound, conjugated, or otherwise associated with a HN-1/anti-tumor composition conjugate. In another specific embodiment the protein transduction domain is the HIV TAT protein (Schwarze et al., 1999), and the addition of the protein transduction domain facilitates delivery to a tumor cell, including a brain tumor cell as this domain permits crossing of the blood-brain barrier. Thus, in this embodiment of the present invention, although the protein transduction domain facilitates delivery to any tissue, the HN-1 peptide of the present invention directs the entire complex specifically to a tumor cell such as a head and neck cancer cell, a breast cancer cell or a brain cancer cell, and the protein transduction domain is primarily an auxiliary means to facilitate that delivery and transduction of the antitumor drug complex. Other protein transduction domains are within the scope of the invention and are known in the art.

A skilled artisan is aware that one could easily screen or test a variant to determine whether the variant still retained tumor targeting properties. That is, in accordance with the methods provided herein such as in the Examples, a HN-1 peptide variant or other internalizing peptide variant may be conjugated to a detectable label, introduced to a cell, and assayed for internalization by the cell. The assay method in a preferred embodiment is fluorescence microscopy, although a skilled artisan is aware that the assay method should be used in accordance with the type of label utilized. In addition or alternative to this in vitro method, an in vivo internalization assay may be used. For example, the variant conjugated to a detectable label is introduced into an animal, such as a nude mouse harboring a tumor or cancerous tissue, and tumor tissue of the animal is assayed for detection of the label. A skilled artisan may use other methods known in the art or variations of these methods to test for targeting of an internalizing peptide, such as HN-1, to a cell.

C. Synthetic Peptides

The present invention describes HN-1, HN-1-related peptides, and other cancer-cell specific peptides for use in various embodiments of the present invention. These peptides have the ability to be specifically uptaken by cancer/tumor cells and not by normal cells. The HN-1 peptide is a 12-mer. However, one can add other sequences to the 12 mer peptide. Also contemplated are other variants and HN-1 related peptides that still retain the ability to translocate through the tumor cell membranes. Such peptides can generally comprise the entire HN-1 sequence, or portions thereof, and be at least four, five, six, seven, eight, nine, ten, eleven, twelve, thirteen, fourteen, fifteen, sixteen, seventeen, eighteen, nineteen, twenty, twenty one, twenty two, twenty three, twenty four, twenty five amino acid residues in length, and may be 5–10, 10–15, 15–20, 20–25, 25–30, 30–35, 35–40, 40–45 or even 55–50 residues or so long.

Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides.

D. Conjugating Methods

In an embodiment of the present invention, an antitumor compound is conjugated to a HN-1 peptide for methods to kill a cancer cell. In another embodiment of the present invention, a detectable label is conjugated to a HN-1 peptide for diagnostic and imaging methods directed to a cancer cell. In a specific embodiment the label is visualized directly. In another embodiment the label is visualized by a secondary means, such as visualization of a second biological entity which detects the label.

In an object of the present invention a HN-1 peptide is conjugated to an antitumor drug or composition. In a specific embodiment the peptide is conjugated to a liposome which contains an antitumor drug or composition. Conjugation means such as those taught by Bauminger and Wilchek (1980) or Nagy et al. (1996), both herein incorporated by reference, are well known in the art. In an embodiment of the present invention, an antitumor drug or composition is conjugated by a carbodiimide. In a specific embodiment of the present invention, an antitumor drug such as doxorubicin is conjugated by 1-ethyl-3-(3-dimethyl-aminopropyl) carbodiimide hydrochloride (EDC) and N-hydroxysuccinimide (NHS), as taught in such references as Arap et al. (1999). Alternatively, a HN-1 peptide is conjugated to an antitumor drug using the method of Brown et al. (1995), which utilizes a Ni(II) complex of a tripeptide $NH_2$-Gly-Gly-His-COOH (SEQ ID NO:2) in the presence of oxidants such as oxone and monoperoxyphthalic acid.

E. Conjugates

Conjugates for labeling a HN-1 peptide for the purpose of detecting or imaging a cancer cell include radiolabels, nuclear magnetic spin-resonance isotopes, fluorescent labels and enzyme tags capable of generating a colored product upon contact with an appropriate substrate. In a specific embodiment, a fluorophore such as FITC or Texas Red fluorescent dye is utilized in methods of the invention. Other fluorophores include: fluorescein, fluorecein diacetate, 5-(and 6)-carboxyfluorescein mixed isomers, 5-carboxyfluorescein single isomer, 6-carboxyfluorescein single isomer, 5-(and 6)-carboxyfluorescein diacetate mixed isomers, 5-carboxyfluorescein diacetate single isomer, 6-carboxyfluorescein diacetate single isomer, 5-(and 6)-carboxyfluorescein succinimidyl ester mixed isomers, 5-carboxyfluorescein succinimidyl ester single isomer, 6-carboxyfluorescein succinimidyl ester single isomer, 5-(and 6)-carboxyfluorescein diacetate succinimidyl ester mixed isomers, 5-carboxyfluorescein diacetate succinimidyl ester single isomer, 6-carboxyfluorescein diacetate succinimidyl ester single isomer, 5-(and 6)-carboxytetraethylrhodamine mixed isomers, 5- carboxytetraethylrhodamine single isomer, 5-(and 6)-carboxytetraethylrhodamine succinimidyl ester mixed isomers, 5-carboxy-tetraethylrhodamine succinimidyl ester single isomer, 6-carboxy-tetraethylrhodamine succinimidyl ester single isomer, 5-(and 6)-carboxy-2i,7i-dichlorofluorescein mixed isomers, 5-(and 6)-carboxy-2i,7i-dichlorofluorescein diacetate(carboxy-DCFDA) mixed isomers, 5-(and 6)-carboxy-2i,7i-dichlorofluorescein diacetate, succinimidyl ester mixed isomers, Alexa fluor 488 dye, Oregon green 488 dye, rhodamine green, orange- and red-fluorescent Alexa fluor dyes, tetramethylrhodamine, lissamine rhodamine B, rhodamine red-X dyes, X-rhodamine, Texas Red-X dyes, naphthofluorescein, LaserPro IR 790, QSY-7 dyes, nonfluorescent malachite green and isosulfan blue, cascade blue dye, coumarin derivatives, naphthalenes, pyrenes, cascade yellow dye, dapoxyl dye, fluorescamine, dialdehydes, such as OPA and NDA, ATTO-TAG reagents, 7-nitrobenz-2-oxa-1,3-diazole (NBD) derivatives, dansyl chloride and other sulfonyl chlorides, succinimidyl esters and carboxylic acids. Other conjugates known in the art may also be utilized.

2. Nucleic Acids

In another embodiment of the present invention there is a DNA segment which encodes SEQ ID NO:1 or a DNA segment comprising a nucleic acid that encodes SEQ ID NO:1. A skilled artisan is aware that multiple codons in the standard genetic code (available in any standard biochemistry or molecular biology textbook known in the art) may encode a particular amino acid of the peptide. However, the third "wobble" position of a codon can be two to four nucleotides of a nucleic acid, depending on the codon, and still encode a particular amino acid. The relatively short length of the HN-1 peptide, being a 12-mer, and the consistency of the first two codon positions of the codons for the amino acids of HN-1 dictates that the number of DNA segments which encode a HN-1 peptide is relatively small.

In another embodiment there is a recombinant vector comprising a DNA segment encoding a HN-1 peptide. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

A. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. Examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki et al., 1998), D1A dopamine receptor gene (Lee et al., 1997), insulin-like growth factor II (Wu et al., 1997), human platelet endothelial cell adhesion molecule-1 (Almendro et al., 1996).

B. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819).

C. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

D. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997).

E. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

F. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

G. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated.

Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

H. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif. ). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

I. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Alternatively, recombinant DNA technology may be employed wherein a nucleotide sequence which encodes a peptide of the invention is inserted into an expression vector, transformed or transfected into an appropriate host cell and cultivated under conditions suitable for expression. A skilled artisan has available many references such as *Current Protocols in Molecular Biology* (Ausubel et al. (eds.)) or *Molecular Cloning: A Laboratory Manual* (Sambrook et al.), herein incorporated by reference for information regarding routine practices for molecular biology including expression of a peptide from an expression vector. The peptide encoded by the nucleotide sequence of the expression vector may be expressed by well known methods in prokaryotes such as *E. coli* or in eukaryotes such as insect cells using baculovirus vectors, in mammalian cells, or in mammalian cells using Vaccinia viral vectors. Expression in *E. coli* may employ the commonly used T7 RNA polymerase/promoter system, or with vectors containing phage lambda regulatory sequences. In embodiments wherein a skilled artisan is concerned with retaining peptide characteristics, such as posttranslational modifications, with producing large quantities of a peptide, especially one which may be toxic, an insect cell system using baculovirus vectors is preferable. Similarly, a skilled artisan may utilize expression of the peptide HN-1 in mammalian cells, having the inherent advantages of maintaining any posttranslational processing capabilities and producing large quantities of proteins. A skilled artisan is aware that transient expression of proteins may be utilized, for example in COS cells, or stably transfected, for example with CHO cells. Finally, Vaccinia virus may be utilized to express the HN-1 peptide, although this expression system utilizes a virus useful for cloning larger fragments than would be required for HN-1 or its derivatives. With any of the known systems for production of the HN-1 peptide by an expression vector, an inducible system may be used, such as tetracycline or galactose systems well known in the art.

3. In vivo Imaging

The invention also provides in vivo methods of imaging cancer using the HN-1 and other cancer specific protein conjugates. The term "in vivo imaging" refers to any non-invasive method that permits the detection of a peptide, or fragment thereof, that specifically binds to cancer cells located in the body of an animal or human subject. In the present invention, as the peptide, or a fragment thereof, is uptaken by the cancer cell specifically the inventors envision detecting the uptake of the peptide by conjugating the peptide or fragment thereof to a suitable detection agent.

In accordance with the isolation of internalizing peptides and detection of cancer by methods of the present invention, a skilled artisan is aware that, an internalizing peptide is utilized to image or diagnose a tumor cell. A skilled artisan, as taught by the methods described herein in the Examples directed to HN-1, may isolate an internalizing peptide which internalizes, identifies or detects a specific cancer cell type. Although the Examples are directed to head and neck cancer cells, such as with squamous cell carcinoma, any cancer cell type may be utilized by the same methods to identify specific internalizing peptides for that cancer cell type. In accordance with this specific embodiment, a skilled artisan can use the methods described herein to identify other peptides which internalize other tumors or cancerous tissue including but not limited to brain cancer, lung cancer, pancreatic cancer, liver cancer, ovarian cancer, cervical cancer, prostrate cancer, etc.

The imaging methods generally involve administering to an animal or subject an imaging-effective amount of a detectable-label conjugated to the HN-1 peptide or fragment thereof, in a pharmaceutically effective carrier, and then detecting the uptake of the labeled HN-1 peptide-label conjugate by the cancerous tissue. The detectable label is preferably a spin-labeled molecule or a radioactive isotope that is detectable by non-invasive methods.

An "imaging effective amount" is an amount of a detectably-labeled HN-1 protein, or fragment thereof, that when administered is sufficient to enable later detection of uptake of the labeled-peptide or fragment to cancer tissue. The effective amount of the peptide-label conjugate is allowed sufficient time to come into contact with the cancer tissue present within the tissues of the patient, and the patient is then exposed to a detection device to identify the detectable label.

Thus, one embodiment of the invention provides the HN-1-dye conjugates or constructs for imaging which have the ability to provide an image of the tumor, for example, through magnetic resonance imaging, x-ray imaging, computerized emission tomography and the like. Elements particularly useful in Magnetic Resonance Imaging ("MRI") include the nuclear magnetic spin-resonance isotopes $^{157}$Gd, $^{55}$Mn, $^{162}$Dy, $^{52}$Cr, and $^{56}$Fe, with gadolinium often being preferred. Radioactive substances, such as technicium$^{99m}$ or indium$^{111}$, that may be detected using a gamma scintillation camera or detector also may be used. Further examples of metallic ions suitable for use in this invention are $^{123}$I, $^{131}$I, $^{131}$I, $^{97}$Ru, $^{67}$Cu, $^{67}$Ga, $^{125}$I, $^{68}$Ga, $^{72}$As, $^{89}$Zr, and $^{201}$Tl.

A factor to consider in selecting a radionuclide for in vivo diagnosis is that the half-life of a nuclide be long enough so that it is still detectable at the time of maximum uptake by the target, but short enough so that deleterious radiation upon the host, as well as background, is minimized. Ideally, a radionuclide used for in vivo imaging will lack a particulate emission, but produce a large number of photons in a 140–2000 keV range, which may be readily detected by conventional gamma cameras.

A radionuclide may be bound to the HN-1 peptide or fragment thereof either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA).

Administration of the labeled HN-1 peptide or fragment thereof, may be local or systemic and accomplished intravenously, intra-arterially, via the spinal fluid or the like. Administration also may be intradermal or intracavitary, depending upon the body site under examination. After a sufficient time has lapsed for the labeled HN-1 peptide or fragment thereof to bind to the diseased tissue, in this case cancer tissue, for example 30 min to 48 h, the area of the subject under investigation is then examined by the imaging technique. MRI, SPECT, planar scintillation imaging and other emerging imaging techniques may all be used. Multiple imaging techniques may be utilized to clarify or confirm detection.

The distribution of the bound radioactive isotope and its increase or decrease with time is monitored and recorded. By comparing the results with data obtained from studies of clinically normal individuals, the presence and extent of the diseased tissue can be determined.

The exact imaging protocol will necessarily vary depending upon factors specific to the patient, and may also depend upon the body site under examination, method of administration, type of label used and the like. The determination of specific procedures is, however, routine to the skilled artisan. Although dosages for imaging embodiments are dependent upon the age and weight of patient, a one time dose of about 0.1 to about 20 mg, more preferably, about 1.0 to about 2.0 mg of labeled HN-1 peptide or fragment thereof per patient is contemplated to be useful.

4. Isolation of Internalizing Peptides

In an embodiment of the present invention there is a method provided herein for isolating an internalizing peptide. Although a skilled artisan is aware that these methods are generally directed to identifying a peptide which internalizes into a tumor or cancerous tissue, a specific example is provided in the Examples directed to identification of HN-1 peptide for use in detecting, imaging or identifying a squamous cell carcinoma. In accordance with this specific embodiment, a skilled artisan can use the methods described herein to identify other peptides which internalize other tumors or cancerous tissue including but not limited to brain cancer, lung cancer, pancreatic cancer, liver cancer, ovarian cancer, cervical cancer, prostrate cancer, etc.

5. Detection of Cancer by Methods of the Present Invention

In an embodiment of the present invention there is a method for detecting cancer. Although the description of the method provided herein is in accordance with that in which a skilled artisan is generally taught how to isolate an internalizing peptide and utilize this peptide to detect a cancer cell, a specific example is described in the Examples regarding isolation of HN-1 peptide as an internalizing peptide and its utilization for detection of squamous cell carcinoma. Specific methods steps may include obtaining an internalizing peptide; conjugating a detectable label to the peptide; administering the conjugated peptide and label to an organism; and detecting binding of the conjugate to cancer cells by suitable detection means.

In an additional embodiment the method for detecting cancer comprises obtaining a peptide library; individually contacting peptides of the library with members of a cell population; assaying for endocytosis of the peptides by the members of the cell population to identify an internalizing peptide; conjugating a detectable label to said peptide; administering the conjugated peptide and label to an organism; and detecting binding of the conjugate to a cell by suitable detection means. Although the cell may be a squamous cell carcinoma cell, including a head and neck cancer cell, it may alternatively be cell from breast cancer, brain cancer, lung cancer, pancreatic cancer, liver cancer, ovarian cancer, cervical cancer, prostrate cancer, etc.

6. Cancer Therapies

In an embodiment of the present invention there is a treatment for cancer utilizing a peptide or fragment of SEQ ID NO:1. The patient to be treated may be an infant, child, adolescent or adult and in a preferred embodiment shows an improvement in at least one symptom of the disease, including a decrease in tumor size.

A wide variety of cancer therapies, known to one of skill in the art, may be used in combination with the tumor cell specific-peptide of the invention. The inventors contemplated using the tumor cell specific-peptide of the invention to achieve specific and targeted delivery of the various chemotherapeutics known in the art to cancer and/or tumor cells. Other embodiments contemplate the use of the tumor cell specific-peptide of the invention to target anticancer drugs in addition to other cancer therapies known in the art. Some of the existing cancer therapies and chemotherapeutic agents are described below. One of skill in the art will recognize the presence and development of other anticancer therapies which can be used in conjugation with the tumor cell specific-peptide of the invention and will further recognize that the use of the tumor cell specific-peptide of the invention will not be restricted to the agents described below.

A. Radiotherapeutic agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In the context of the present invention radiotherapy may be used in addition to using the tumor cell specific-peptide of the invention to achieve cell-specific cancer therapy.

B. Surgery

Surgical treatment for removal of the cancerous growth is generally a standard procedure for the treatment of tumors and cancers. This attempts to remove the entire cancerous growth. However, surgery is generally combined with chemotherapy and/or radiotherapy to ensure the destruction of any remaining neoplastic or malignant cells. Thus, in the context of the present invention surgery may be used in addition to using the tumor cell specific-peptide of the invention to achieve cell-specific cancer therapy.

C. Chemotherapeutic Agents

These can be, for example, agents that directly cross-link DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include adriamycin (also known as doxorubicin), VP-16 (also known as etoposide), verapamil, podophyllotoxin, and the like. Widely used in clinical setting for the treatment of neoplasms, these compounds are administered through bolus injections intravenously at doses ranging from 25–75 mg/m$^2$ at 21 day intervals for adriamycin, to 35–100 mg/m$^2$ for etoposide intravenously or orally.

Antibiotics

Doxorubicin

Doxorubicin hydrochloride, 5,12-Naphthacenedione, (8s-cis )-10-((3-amino-2,3,6-trideoxy-a-L-lyxo-hexopyranosyl)oxy)-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Daunorubicin

Daunorubicin hydrochloride, 5,12-Naphthacenedione, (8S-cis)-8-acetyl-10-((3-amino-2,3,6-trideoxy-a-L-lyxo-hexanopyranosyl)oxy)-7,8,9,10-tetrahydro-6,8,11-trihydroxy-10-methoxy-, hydrochloride; also termed cerubidine and available from Wyeth. Daunorubicin intercalates into DNA, blocks DNA-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m²/day (30 mg/m² for patients older than 60 yr.) for 1, 2 or 3 days every 3 or 4 wk or 0.8 mg/kg/day for 3 to 6 days every 3 or 4 wk; no more than 550 mg/m² should be given in a lifetime, except only 450 mg/m² if there has been chest irradiation; children, 25 mg/m² once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m², 20 mg/m², 30 mg/m², 50 mg/m², 100 mg/m², 150 mg/m², 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course these dosages are exemplary, and any dosage in-between these points is also expected to be of use in the invention.

Mitomycin

Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg., 20 mg., or 10 mg. I.V., the maximal serum concentrations were 2.4 mg./mL, 1.7 mg./mL, and 0.52 mg./mL, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D

Actinomycin D (Dactinomycin) (50-76-0); $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m², 150 mg/m², 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

Bleomycin

Bleomycin is a mixture of cytotoxic glycopeptide antibiotics isolated from a strain of *Streptomyces verticillus*. It is freely soluble in water.

Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

Bleomycin may be given by the intramuscular, intravenous, or subcutaneous routes.

Miscellaneous Agents

Cisplatin

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15–20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg//m$^2$. Of course, all of these dosages are exemplary, and any dosage in-between these points is also expected to be of use in the invention.

Cisplatin is not absorbed orally and must therefore be delivered via injection intravenously, subcutaneously, intra-tumorally or intraperitoneally.

In certain aspects of the current invention cisplatin is used in combination with emodin or emodin-like compounds in the treatment of non-small cell lung carcinoma. It is clear, however, that the combination of cisplatin and emodin and or emodin-like compounds could be used for the treatment of any other neu-mediated cancer.

VP16

VP16 is also know as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200–250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

Tumor Necrosis Factor

Tumor Necrosis Factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

Plant Alkaloids

Taxol

Taxol is an experimental antimitotic agent, isolated from the bark of the ash tree, Taxus brevifolia. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisolone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisolone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisolone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

Vinblastine

When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$ 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

Alkylating Agents

Carmustine

Carmustine (sterile carmustine) is one of the nitrosoureas used in the treatment of certain neoplastic diseases. It is 1,3bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisolone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$ 40 mg/m$^2$ 50 mg/m$^2$ 60 mg/m$^2$ 70 mg/m$^2$ 80 mg/m$^2$ 90 mg/m$^2$ 100 mg/m$^2$. The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject

Melphalan

Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-(bis(2-chloroethyl)amino)-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of ~2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject.

Cyclophosphamide

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl)phosphoramidic dichloride ((ClCH$_2$CH$_2$)$_2$N—POCl$_2$) in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

Chlorambucil

Chlorambucil (also known as leukeran) is a bifunctional alkylating agent of the nitrogen mustard type that has been found active against selected human neoplastic diseases. Chlorambucil is known chemically as 4-(bis(2-chlorethyl)amino)benzenebutanoic acid.

Chlorambucil is available in tablet form for oral administration. It is rapidly and completely absorbed from the gastrointestinal tract. After single oral doses of 0.6–1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remington's Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Busulfan

Busulfan (also known as myleran) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

Lomustine

Lomustine is one of the nitrosoureas used in the treatment of certain neoplastic diseases. It is 1-(2-chloro-ethyl)-3-cyclohexyl-1nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 $mg/m^2$ to 100 $mg/m^2$, about half of the radioactivity given was excreted in the form of degradation products within 24 hours.

The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 $mg/m^2$ as a single oral dose every 6 weeks. In individuals with compromised bone marrow function, the dose should be reduced to 100 $mg/m^2$ every 6 weeks. When lomustine is used in combination with other myelosuppressive drugs, the doses should be adjusted accordingly. It is understood that other doses may be used for example, 20 $mg/m^2$ 30 $mg/m^2$, 40 $mg/m^2$, 50 $mg/m^2$, 60 $mg/m^2$, 70 $mg/m^2$, 80 $mg/m^2$, 90 $mg/m^2$, 100 $mg/m^2$, 120 $mg/m^2$ or any doses between these figures as determined by the clinician to be necessary for the individual being treated.

D. Gene Therapy Administration

In an embodiment of the present invention the approach utilizing HN-1 peptide conjugated to an anti-tumor composition is administered in conjunction with gene therapy. For gene therapy, a skilled artisan would be cognizant that the vector to be utilized must contain the gene of interest operatively limited to a promoter. For antisense gene therapy, the antisense sequence of the gene of interest would be operatively linked to a promoter. One skilled in the art recognizes that in certain instances other sequences such as a 3' UTR regulatory sequences is useful in expressing the gene of interest. Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds. A sufficient amount of vector containing the therapeutic nucleic acid sequence must be administered to provide a pharmacologically effective dose of the gene product.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

It is possible that cells containing the therapeutic gene may also contain a suicide gene (i.e., a gene which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. Thus, expression of the therapeutic gene in a host cell can be driven by a promoter although the product of said suicide gene remains harmless in the absence of a prodrug. Once the therapy is complete or no longer desired or needed, administration of a prodrug causes the suicide gene product to become lethal to the cell. Examples of suicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

respective administrations. In addition the treatments may be combined along with radiotherapeutic treatments also.

It also is conceivable that more than one administration of either radiotherapeutic and/or the HN-1 peptide or fragment thereof with one or more of the anticancer drugs may be required. Various combinations may be employed, where the HN-1 peptide conjugated to one chemotherapeutic or radiotherapeutic agent is designated as "A" and the HN-1 peptide conjugated to another chemotherapeutic or radiotherapeutic agent is designated as "B", or alternatively, the HN-1 peptide conjugated to one chemotherapeutic or radiotherapeutic agent is designated as "A" and the chemotherapeutic or radiotherapeutic agent is designated as "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

The method of cell therapy may be employed by methods known in the art wherein a cultured cell containing a copy of a nucleic acid sequence or amino acid sequence for therapy of cancer is introduced.

In a specific embodiment of the present invention, the peptide of HN-1 comprising SEQ ID NO:1 is associated with, either directly or indirectly, a vector containing or comprising a nucleic acid sequence for gene therapy. In a specific embodiment the nucleic acid for therapy is p53, which is often mutated in head and neck squamous cell carcinomas. Alternatively, as is taught be Foster et al., 1999, herein incorporated by reference, a compound to stabilize the DNA binding domain of p53 in an active conformation is delivered via an HN-1 peptide of the present invention to enable a mutant p53 in a tumor cell to activate transcription and slow tumor growth. In a specific embodiment the compound for stabilization comprises a hydrophobic group containing at least one cyclic group joined by a linker to an ionizable group, such as an amine. The HN-1 peptide of the present invention may be joined by direct or indirect means to such an active compound for p53 stabilization.

In another specific embodiment of the present invention there is a treatment for thyroid cancer, a head and neck cancer, utilizing gene therapy with a sodium/iodide symporter gene, such as described by Mandell et al. (1999) or Lazar et al. (1999), both herein incorporated by reference. NIS controls uptake of iodide by coding for a protein on the surface of thyroid cells. Radioactive iodide, such as $^{123}$I or $^{131}$I, is administered to a patient in conjunction or following administration of a HN-1 peptide bound by some means to a vector NIS-containing nucleic acid, and the iodide is taken in by the cancerous thyroid tumor cells and killed.

E. Combinations

Often combinations of the various cancer therapies described are used for more effective tumor cell killing. Thus, it is contemplated that one would administer to the patient HN-1 peptide conjugated to one or more chemotherapeutic agents. These may be administered either at the same time, within about 6–12 hours of each other, within about 12–24 hours of each. In some situations, it may be desirable to extend the time period for treatment significantly, however, where several days (2, 3, 4, 5, 6 or 7) to several weeks (1, 2, 3, 4, 5, 6, 7 or 8) lapse between the Other combinations and the use of more than two of the HN-1 peptide conjugated chemotherapeutic agents are also contemplated.

In addition, the tumor-specific anticancer regimen can be administered to a patient in conjunction with a surgical procedure such as the excision of a tumor, and/or with immunotherapy, gene therapy, radiotherapy, chemotherapy, and/or local heat therapy. The inventors contemplate that the dosage of the irradiation for the radiotherapy, and or the dosage of the compound for the chemotherapy, will be much lower when used in conjunction with the therapy of the present invention. This in turn will lower the side effects of the standard anti-cancer therapies and simultaneously achieve a better and more effective anti-cancer therapy. The exact dosages and regimens can be suitably determined and altered by one of ordinary skill in the art.

F. Formulations and Routes for Administration to Patients

Where clinical applications are contemplated, it will be necessary to prepare pharmaceutical compositions of the HN-1 peptide and its conjugated drug or labels in a form appropriate for the intended application. Generally, this will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Supplementary active ingredients also can be incorporated into the compositions.

The active compositions of the present invention may include classic pharmaceutical preparations. Administration of these compositions according to the present invention will be via any common route so long as the target tissue is available via that route. Although, the intravenous route is a preferred embodiment, other routes of administration are contemplated. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy administration by a syringe is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The carrier also can be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035–1038 and/or 1570–1580). Some variation in dosage will necessarily occur depending on the condition of the subject being treated. The person responsible for administration will, in any event, determine the appropriate dose for the individual subject.

The HN-1 peptide may be conjugated to an anticancer drug and may be formulated within a therapeutic mixture to comprise about 0.0001 to 1.0 milligrams, and/or about 0.001 to 0.1 milligrams, and/or about 0.1 to 1.0 and/or even about 10 milligrams per dose and/or so. Multiple doses can also be administered.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including creams.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation. Various commercial nasal preparations are known and/or include, for example, antibiotics and/or antihistamines and/or are used for asthma prophylaxis.

Additional formulations which are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25–60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

G. Kits

In further embodiments, the invention provides cancer-therapeutic kits, cancer-detection kits and or cancer-imaging kits for use in detecting and imaging cancer and tumor cells and tissues, both in vivo, e.g., in a patient, and in vitro, e.g., in biological samples. Such kits will generally comprise a pharmaceutically acceptable composition comprising a peptide that targets a tumor cell, such as HN-1, or a fragment thereof, bound to a suitable detectable label. Also included will be a suitable detection means for the peptide conjugated to the label. The detectable label is such that it can be identified by non-invasive means for in vivo applications.

As the peptide can comprise the HN-1 peptide or fragments thereof, these peptides may be provided in the kit. The kits may further comprise a suitably aliquoted amounts of the peptide that can targets the tumor cell, and a standard curve may further be prepared for a detection assay.

In certain embodiments, the HN-1 peptide or the fragments thereof either are bound to the detectable label and may be further be bound to a solid support, such as a column matrix or well of a microtitre plate.

A number of exemplary labels are known in the art and all such labels may be employed in connection with the present invention. Radiolabels, nuclear magnetic spin-resonance isotopes, fluorescent labels and enzyme tags capable of generating a colored product upon contact with an appropriate substrate are suitable examples. Detectable labels that are associated with or attached to a secondary binding ligand are also contemplated.

The kits of the invention will generally comprise one or more containers into which the biological agents are placed and, preferably, suitably aliquoted. The components of the kits may be packaged either in aqueous media or in lyophilized form.

The container means of the kits will generally include at least one vial, test tube, flask, bottle, or even syringe or other container means, into which the peptide conjugated to the label may be placed, and preferably, suitably aliquoted. Where a second or third detectable label, binding ligand or additional component is provided, the kit will also generally contain a second, third or other additional container into which this label, ligand or component may be placed.

The kits of the present invention will also typically include a means for containing the peptide conjugated to the label, additional labels and any other reagent containers in close confinement for commercial sale. Such containers may include injection or blow-molded plastic containers into which the desired vials are retained.

6. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell Lines

All HNSCC cell lines were established at M. D. Anderson Cancer Center. DU148 and SW480 cell lines were obtained from American Type Culture Collection (Bethesda, Md.) and normal human fibroblast AG04354 was obtained from Coriell Cell Culture Facility (Bethesda, Md.). The above cell lines were maintained in DMEM/F-12 medium with 10% FBS, 2 mM L-glutamine and antibiotics at 37° C. in 5% $CO_2$ environment. HOK16B was were maintained in Keratinocyte-SFM media 17005-042 (Gibco-BRL; Bethesda, Md.) supplemented with EGF and bovine pituitary extract.

Peptide-Display Library Screening

M13 phage peptide library PhD-12 displaying random 12-mer peptides was obtained from New England BioLabs (Beverly, Mass.). $2.5 \times 10^{12}$ plaque forming units were incubated with $5 \times 10^6$ MDA167Tu cells in growing medium at 37° C. in 5% $CO_2$ environment for 3 h. Nonspecific internalization of phages were blocked by incubating in growth medium, which also ensures that the peptides isolated would not be degraded in its presence of serum during drug delivery. The internalized phages were recovered by lysing with TX-100 (1%) for 30 min at 37° C. and amplified using the E. coli strain ER2537. Although TX-100 could not lyse the nuclei, ionic detergents capable of disrupting nuclear membrane were avoided as they inactivate the phage. To eliminate phage that became internalized after interacting with constitutively expressed molecules, the above isolated phages were incubated with normal human fibroblasts (NHFs), and the supernant containing unbound phages was recovered and the phages were amplified. Finally, recovered phages were subjected to 5 rounds of MDA167Tu-selection and 3 rounds of NHF-subtraction. DNA sequencing of 12 randomly picked phages revealed that they encoded an identical, novel peptide, TSPLNIHNGQKL (SEQ ID NO:1). The occurrence of vector sequences flanking the peptide-encoding region and the exclusive occurrence of T/G nucleotide at every third base of each codon within the peptide-encoding region (as engineered) confirmed that the phages were derived from the library. Sequence alignment was performed using NCBI-based BLAST or FASTA. MDA167Tu cells exhibited 10.3-fold greater internalization potential for TSPLNIHNGQKL-phage than NHFs. BLAST search revealed no homology with previously determined sequences.

Gel Electrophoresis

Cell lysates suspended in Sample Buffer (0.12M Tris (pH 6.8), 2% SDS, 20% glycerol and 10% b-mercaptoethanol) were separated by 17.5% SDS-PAGE (Hensey et al., 1994) and viewed using UV light. The images were captured digitally using Kodak Digital Science 1D software.

Peptide Synthesis

Peptides were synthesized and purified by reverse-phase HPLC to >95% purity (Research Genetics, Huntsville, Ala.). A fluorescent label was added at the N-terminus, and the carboxyl terminus was capped with an amide group. Mass spectrometry confirmed the predicted mass. Peptides were further purified by gel electrophoresis, excised, dialyzed, lyophylized (in dark), resuspended in PBS, and filter-sterilized.

Fluorescence Microscopy

Cells were fixed with 3% N-formyl paraformaldehyde, mounted using Anti-Fade (Molecular Probe; Eugene, Oreg.), and viewed using Nikon fluorescence microscope Eclipse E400. Images were captured digitally and analyzed using Metamorph version 3.6a software. To determine fluorescence intensity, the extent of autofluorescence was subtracted from the observed intensity.

Subcellular Fractionation Study

Subcellular fractionation was performed as described (Lee et al., 1987). Isolation of nuclear, cytoplasmic, and cell membrane fractions was confirmed by Western blot analysis using antibodies specific for human retinoblastoma protein, glutathione transferase and GLUT-1 glucose transporter protein, respectively. Individual fractions were electrophoresed and viewed. An equivalent amount of each fraction was loaded Protease Protection Assay Peptide-incubated cells were rinsed with PBS, scraped, pelleted by centrifuging at 2000 rpm, and resuspended in 100 ul of PBS. To lyse, cells were freeze-thawed 10 times using dry ice. After treating with chymotrypsin (10 units) for 5 min at 25° C., the enzyme was inactivated with SDS (1%). Samples were suspended in Sample Buffer, electrophoresed, and viewed. It was noted that no peptide was detected in cell extracts when incubated with chymotrypsin-pre-treated peptide.

Primary Tissue Analysis

A biopsy of human invasive squamous cell cancer was rapidly frozen in OCT blocks and 4 micron-thick cryostat sections were prepared. No fixative or embedding material was used to avoid modifying molecules that may interact with HN-1. As H&E dyes fluoresced under the wavelength used for viewing fluorescein, an untreated adjacent section was incubated with FITC-HN-1. After incubating with FITC-HN-1 (2.6 uM) in PBS-GLY (PBS containing 10 mM glycine and 0.01% BSA) for 12 h at 25° C. in a sealed environment, slides were rinsed in PBS-GLY for 48 h with frequent changes. Samples were mounted and viewed as described herein.

Animal Experiment

Five week-old nude mice (Harlan Sprague-Dawley) purchased from Parke-Davis (Morris Plains, N.J.) were subcutaneously injected with $5 \times 10^6$ tumor cells suspended in PBS. Mice harboring tumors (~0.5 cm in diameter) were randomized into separate groups (5 per group) and peptides or other indicated agents ($2.6 \times 10^{-8}$ mole) suspended in 100 $\mu$l of PBS were injected at the tail vein. All mice were maintained under an identical condition. After 48 h, mice were euthanized and their tissues recovered to prepare cryostat sections. Autofluorescence was suppressed with Eriochrome Black T (1.3%). For peptide extraction, specimens (harvested after perfusion with PBS) of equivalent mass were frozen in liquid nitrogen, pulverized, and resuspended in Lysis Buffer (50 mM Tris (pH 7.4), 250 mM NaCl, 5 mM EDTA, 0.5% NP40 and protease inhibitors). After centrifuging to remove nuclei and other cell debris, the supernatant was electrophoresed and viewed as described above. For the extract analysis, mice were injected with $2.6 \times 10^{-7}$ mole of FITC-HN-1. All animal protocols were reviewed and approved by the institution's Animal Care and Use Committee.

In vitro Internalization Assay

To view, HN-1 peptide was conjugated with FITC or Texas Red fluorescent dye. For fluorescent microscopy, cells were grown in 8-chamber slides and incubated with the peptide for 48 h inside the incubator, fixed, and viewed using a Nikon fluorescence microscope. Images were captured digitally and viewed using Microsoft PowerPoint software. The lysate of peptide-incubated cells was electrophoresed through a denaturing polyacrylamide gel to view the internalized peptide. Subcellular fractionation assay was performed through the following: cell membrane of peptide-incubated cells was disrupted in hypotonic solution using a Dounce homogenizer. After isolating nuclei by centrifuging at 2000 rpm, the cell membrane fraction was isolated by ultracentrifuging the remainder at 35,000 rpm for 90 min at 37° C. The supernatant was lyophilized and resuspended in PBS. Individual fractions were separated through a denaturing gel and viewed using LTV (short wave) light.

Primary HNSCC Tissue Analysis

Histological sections containing both the normal human squamous and HNSCC cells was incubated with the peptide in PBS containing glycine (IOMM) for 12 h at 25° C. After washing for 48 h in PBS at 4° C., the sample was mounted and viewed as described above.

In vivo Internalization Assay

Peptide was intravenously injected at the tail of a nude mouse harboring a human HNSCC xenograft. After 48 h, the mouse was euthanized using $CO_2$ and tumor and other tissues were resected and frozen in OCT. Histological sections of the samples were prepared and viewed using fluorescence microscopy as described above.

Example 2

Isolation and Screening of the Peptide

The isolation of the peptide of the invention was carried out by screening a random peptide-display library. Since the ability to translocate across the cell membrane is critical for drug delivery, the present inventors sought peptides that can be internalized by cells. Furthermore, the inventors sought peptides that could be internalized by cancer and or tumor cells rather than by normal non-cancerous tissue.

The inventors screened an M13 single-stranded bacteriophage-based random peptide-display library using the human head and neck squamous cell cancer (HNSCC) cell line, MDA167Tu. The screening method was based on the ability of the HNSCC cells to uptake the peptides by endocytosis at 37° C.

The screening of the library was performed in growth medium to ensure that the peptide isolated was not degraded in the presence of serum during drug delivery. A novel peptide was isolated bearing the sequence, Thr-Ser-Pro-Leu-Asn-Ile-His-Asn-Gly-Gln-Lys-Leu (TSPLNIHNGQKL), (SEQ ID NO. 1). This peptide also is referred to as the HN-1 peptide herein. The MDA167Tu cells exhibited an ~10-fold greater internalization potential for TSPLNIHNGQKL-phage than normal human fibroblasts (NHFs) which were used for subtraction.

The Asn-Gly-Gln sequence contained in the peptide isolated in this invention, Thr-Ser-Pro-Leu-Asn-Ile-His-Asn-Gly-Gln-Lys-Leu, resembles Asn-Gly-Arg (NGR) cell adhesion motif but the possibility of the two motifs interacting with a common receptor is unlikely given that a single conservative substitution abolished the binding property in the case of the RGD motif (RGD→RGE) (Arap et al., 1998; Pasqualini et al., 2000; Cherny et al., 1993).

Internalization of HN-1 peptide was directly tested using a synthetic peptide. To mimic drug delivery, HN-1 was conjugated to fluorescein, a complex organic molecule composed of multiple ringed structures and a carboxylic acid group with ~44% of the mmolecular mass of paclitaxel (Taxol) (Nicolaou et al., 1994). After incubating with FITC-HN-1 for 48 h, 5 of 6 of human HNSCC cell lines examined (MDA138Tu, MDA159Tu, MDA167Tu, MDA686Tu, MDA1986Tu, MDA177Tu) exhibited internal fluorescence, although little fluorescence was observed with similarly incubated human papilloma virus-immortalized normal human oral keratinocytes (HOKs) (FIGS. 1A, 1B). The fluorescence intensity was time- and dose-dependent.

The distribution of cells with respect to fluorescence intensity for each cell line is shown in FIG. 1b. Internal fluorescence was also observed when the cells were not fixed, excluding the possibility of the peptide being artifactually internalized during fixing. The viability of fluorescing cells was confirmed by trypan blue exclusion. None of the cell lines exhibited autofluorescence (see FIG. 1a for untreated MDA177Tu cells). When the lysate of FITC-HN-1 incubated MDA177Tu cells was electrophoretically separated and viewed under UV light, intact peptide was detected (lane 4 of FIG. 1D; lane 3 of FIG. 1E). Degradation by an externally applied protease occurred only with prior cell lysis, confirming the internalization of FITC-HN-1 (FIG. 1D). The facts that fluorescein did not get internalized (FIG. 1a), that little dissociation of fluorescein from the peptide was detected when the medium of FITC-HN-1-incubated cells was analyzed (not shown), and that little labeling occurred after incubating with fluorescein and HN-1 separately (FIG. 1a) suggest that the possibility of the observed fluorescence being due to the uptake of dissociated fluorescein is unlikely.

Both the fluorescence microscopy data (FIGS. 1A–C) and subcellular fractionation data (FIG. 1E) indicate that the internalized HN-1 was present mainly in the cytoplasm, which is consistent with the fact that HN-1-displaying phages were isolated from the cytoplasm during the screening. Under higher magnification, a punctate fluorescence pattern was observed, indicating that HN-1 may be compartmentalized after the entry into the cell (FIG. 1C). The punctate pattern is similar to that previously observed with internalized epidermal growth factor (EGF), which enters via receptor-mediated endocytosis (Beguinot et al., 1986).

Internalization of HN-1 also was observed after conjugating to Texas Red (FIG. 1A). As fluorescein (FIG. 1A) and Texas Red are impermeable, the dyes themselves could not have mediated the internalization of HN-1. Shifting the relative position of HN-1 with respect to the peptide GGG TSPLNIHNGQKLGGGS (HN-2) (SEQ ID NO:3) or GSR-RASVTSPLNIHNGQKL (HN-3) (SEQ ID NO:4) did not inhibit its internalization but jumbling the sequence did (NQHSKNTLLIGP (HN-J) (SEQ ID NO:5)) (FIG. 1A, panel 3), suggesting that HN-1 internalization is 'position-independent' but 'sequence-dependent'. The uptake of FITC-conjugated HN-2 or HN-3 excludes the possibility that the ability of HN-1 to enter cells is a property acquired through its juxtaposition with fluorescein.

To determine if the internalization of HN-1 occurs specifically, a competition assay was performed. Whereas the internalization of FITC-HN-1 was blocked by unlabeled HN-1 when provided in excess, no such inhibition occurred with an irrelevant peptide (FIG. 1F). This indicates that HN-1 uptake may require a specific interaction with a heterologous molecule, which may be a cell-associated molecule or a molecule present in the growth medium.

Intriguingly, FITC-HN-1 incubated DU147 human prostate cancer cells or SW480 human colon cancer cells displayed little fluorescence (shown for 48 h; FIG. 1B) even after a prolonged incubation (96 h), indicating that HN-1 uptake does not occur ubiquitously and that HN-1 entry may not be mediated by a constitutively expressed molecule. The inventors also confirmed that the lack of HN-1 uptake was not due to degradation of the peptide in the medium. The latter possibility, however, appears unlikely given that HN-1 internalization also occurred in PBS.

Intriguingly, DU145 human prostate, SW480 human colon or U373MG human astrocytoma cells displayed little fluorescence (FIG. 1b) even after a prolonged (96–120 h) incubation with FITC-HN-1, indicating that HN-1 uptake does not occur ubiquitously. That the lack of its uptake was not due to the degradation of peptide in the medium was independently confirmed (not shown). The results also suggest that not all actively dividing cells can internalize HN-1.

An in situ peptide-binding assay performed on cryostat sections prepared from a biopsy sample of human invasive HNSCC, which contained invasive malignant cells as well as adjacent nonmalignant squamous epithelium, showed the preferential binding of FITC-HN-1 to invasive cancer cells (FIG. 2). The inability of fluorescein or FITC-HN-J to bind (FIG. 2) suggests that the binding of FITC-HN-1 was mediated by HN-1.

Since the internalization of HN-1 is restricted to certain cancer cell types and is not a property of all dividing cells the inventors envision using HN-1 for targeted drug delivery to specific cancer cell types. This property of HN-1 is critical as most of the presently used chemotherapeutics (for example, DNA crosslinking agents like cisplatin or inhibitors of DNA metabolism like methoxtrexate) target dividing cells nondiscrimately. This results in the many varied side effects of the chemotherapeutic agents.

Example 3

Localization of HN-1

In vivo experiments were performed to determine if intravenously administered HN-1 localizes to tumor tissues. Nude mice harboring subcutaneously established MDA177Tu-derived tumor xenografts were injected intravenously with FITC-HN-1. (FIGS. 3A and 4B). As in in vitro, little labeling of the nuclei was observed in vivo. The untreated tumor cells did not autofluoresce (FIG. 3A). The presence of intact peptide was confirmed by the electrophoretic analysis of tumor extract (FIG. 3B). As the latter was prepared from a FITC-HN-1-injected mouse harboring MDA167Tu-derived xenograft, it suggested that HN-1 can be internalized by xenografts derived from multiple HNSCC cell lines. Little labeling of tumor cells was observed after injecting equimolar concentration of fluorescein, FITC-HN-J, or fluorescein and unlabeled HN-1 separately into mice with size-matched tumors (FIG. 3A).

FITC-HN-1 failed to label xenografts derived from prostate cancer cell line DU145 cells (FIG. 3A), which poorly internalizes the peptide in vitro (FIG. 1B). Importantly, brain, heart, lung, kidney and liver from FITC-HN-1-injected tumor-bearing mice showed little labeling (FIGS. 3B, 3C). A similar result was also obtained with FITC-HN-1-injected tumor-free mice, suggesting that the inefficient labeling was not due to peptide depletion by the tumor. The alternate possibility of it being due to rapid peptide degradation in these tissues or due to the inability of the peptide to recognize the murine homologue of its cognate receptor cannot be excluded.

To determine if HN-1 infiltrated tumor tissue, histological sections prepared from the center of the xenograft of FITC-HN-1 injected mice shown in panel 6 of FIG. 3A were examined. Hematoxylin and eosin (H&E) staining showed that the lower half was comprised of dispersed tumor cells, whereas the remainder contained tumor cells compartmentalized (FIG. 4B) An adjacent section from the treated mice showed fluorescing tumor cells (FIG. 4B). It was noted that the fluorescence was due to tumor cells, not to keratins (compare panels 2 and 3 of FIG. 4B). Fluorescence appeared ubiquitous as the tumor cells located centrally as well as peripherally (FIG. 4B). Labeling of tumor cells located at the interior suggests that FITC-HN-1 is capable of penetrating tumor tissues. Histological sections prepared from other points throughout the tumor from the treated mice also showed fluorescing tumor cells.

Example 4

Significant of Targeting of HN-1 to Tumor Cells

Previously, it was shown that drugs conjugated to tumor vasculature-specific peptides could eliminate tumors indirectly by destroying endothelial vessels. However, as tumors smaller than 1 mm$^3$ can persist through nutrients obtained from adjacent normal blood vessels, the task of eliminating the remaining tumor still remains (Folkman, 1990). The isolation of HN-1 will allow health care providers the ability to provide the necessary dose of a drug to destroy tumors without being restricted by the occurrence of harmful side effects to other cells. The potential of HN-1 to be utilized as a shuttle is further strengthened by the fact that it is nontoxic (no histological evidence of organotoxicity was observed in HN-1 injected mice), stable in vivo, protects its "cargo" during transit, and accumulates efficiently within the tumor in 48 hours. If the internalized HN-1 is compartmentalized in endosomes, the release of conjugated drugs to cytosol may need to rely on the endosomal degradation of the peptide (Ryser et al., 1988). The other potential uses of HN-1 discussed herein include tumor diagnosis, imaging, or radioablation. It may also provide tumor-specificity to gene transfer approaches[12]; this is supported by the observation that HN-1 can enhance the transfer of liposome-DNA complexes into HNSCC cells.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Almendro et al., "Cloning of the human platelet endothelial cell adhesion molecule-1 promoter and its tissue-specific expression. Structural and functional characterization," *J Immunol.* 157(12):5411–5421, 1996.

Arap, Pasqualini, Ruoslahti, "Cancer treatment by targeted drug delivery to tumor vasculature in a mouse model," *Science,* 279:377–380, 1998.

Ausubel, F. M., Brent, R., Kingston, R. E., Moore, D. D., Seidman, J. G., Smith, J. A., and Struhl, K. Current Protocols in Molecular Biology. Current Protocols (Greene & Wiley). Harvard Medical School., 1991.

Barany and Merrifield, "A chromatographic method for the quantitative analysis of the deprotection of dithiasuccinoyl (Dts) amino acids" *Anal Biochem.* 95(1):160–70, 1979.

Barry, Dower, Johnston, "Toward cell-targeting gene therapy vectors: selection of cell-binding peptides from random peptide-presenting phage libraries," *Nature Med.,* 2:299–305, 1996.

Beguinot et al., "Functional studies on the EGF receptor with an antibody that recognizes the intracellular portion of the receptor," *J Biol Chem.;* 261(4):1801–1807, 1986.

Beguinot, Werth, Ito, Richert, Willingham, Pastan, "Functional studies on the EGF receptor with an antibody that recognizes the intracellular portion of the receptor," *J. Biolog. Chem.,* 261(4):1801–7, 1986.

Carbonelli et al. "A plasmid vector for isolation of strong promoters in *Escherichia coli,*" *FEMS Microbiol Lett.* 177(1):75–82, 1999.

Chandler et al., "RNA splicing specificity determined by the coordinated action of RNA recognition motifs in SR proteins," *Proc Natl Acad Sci USA.* 94(8):3596–3601, 1997.

Cherny et al., "Site-directed mutagenesis of the arginine-glycine-aspartic acid in vitronectin abolishes cell adhesion." *J Biol Chem.* 268(13):9725–9729, 1993.

Cherny, R. C., Honan, M. A. and Thiagarajan, P. Site-directed mutagenesis of the arginine-glycine-aspartic acid in vitronectin abolishes cell adhesion. *J. Biol. Chem.* 268, 9725–9729 (1993).

Clayman, el-Naggar, Roth, Zhang, Goepfert, Taylor, Liu, "In vivo molecular therapy with p53 adenovirus for microscopic residual head and neck squamous carcinoma," *Cancer Res.,* 55(1):1–6, 1995.

Cocea, L. "Duplication of a region in the multiple cloning site of a plasmid vector to enhance cloning-mediated addition of restriction sites to a DNA fragment," *Biotechniques.* 23(5):814–816, 1997.

Current Protocols in Molecular Biology. Ed. F. M. Ausubel et al., 1996.

D'Souza, Ginsberg, Plow, "Arginyl-glycyl-aspartic acid (RGD): a cell adhesion motif," *Trends Biochem. Sci.,* 16(7):246–50, 1991.

Dvorak, Nagy, Dvorak, "Structure of solid tumors and their vasculature: implications for therapy with monoclonal antibodies," *Cancer Cells,* 3(3):77–85, 1991.

Folkman J. "Endothelial cells and angiogenic growth factors in cancer growth and metastasis. Introduction," *Cancer Metastasis Rev.* 9(3):171–174, 1990.

Folkman J. "What is the evidence that tumors are angiogenesis dependent?" *J Natl Cancer Inst.* 82(1):4–6, 1990.

Folkman, J. "Tumor Angiogenesis," *Adv. Cancer Res.,* 43:175–230, 1985.

Folkman, J. What is the evidence that tumors are angiogenesis dependent? *J. Natl. Cancer Inst.* 82, 4–6 (1990).

Gatsakis, J. G. in *Comprehensive management of Head and Neck Tumors* (eds. Thawley, S. E. and Panje, W. R.) 480–515 (W. B. Saunders Company, Philadelphia, 1987).

Hensey, Hong, Durfee, Qian, Lee, Lee, "Identification of discrete structural domains in the retinoblastoma protein. Amino-terminal domain is required for its oligomerization," *J. Biol. Chem.,* 269(2):1380–1387, 1994

Hoekman, van der Vijgh, Vermorken, "Clinical and preclinical modulation of chemotherapy-induced toxicity in patients with cancer,"*Drugs.,* 57(2):133–55, 1999.

Kraus et al., "Alternative promoter usage and tissue specific expression of the mouse somatostatin receptor 2 gene," *FEBS Lett.,* 428(3):165–170, 1998.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," *J Biol Chem.,* 274(12):8282–8290, 1999.

Lee et al., "Activation of beta3-adrenoceptors by exogenous dopamine to lower glucose uptake into rat adipocytes," *J Auton Nerv Syst.* 74(2–3):86–90, 1997.

Lee, Shew, Hong, Sery, Donoso, Young, Bookstein, Lee, "The retinoblastoma susceptibility gene encodes a nuclear phosphoprotein associated with DNA binding activity," *Nature,* 329(6140):642–5, 1987.

Levenson et al., "Internal ribosomal entry site-containing retroviral vectors with green fluorescent protein and drug resistance markers," *Hum Gene Ther.* 20;9(8):1233–1236, 1998.

Lowenthal and Eaton, "Toxicity of chemotherapy," *Hematol. Oncol. Clinics,* 10(4):967–90, 1996.

Merrifield, G. "Solid phase synthesis" *Science* 232(4748):341–7 (1986).

Nicolaou et al., "Novel Chemistry of Taxol. Retrosynthetic and Synthetic Studies," *J. Chem. Soc., Chem. Commun.,* pp. 295–296, 1994.

Nicolaou et al., "Synthesis of Novel Taxoids," *J. Am. Chem. Soc.,* 116:pp. 1591–1592, 1994.

Nicolaou et al., "Total Synthesis of Taxol," *Nature,* 367:pp. 630–634, 1994.

Nicolaou, K. C. et al., Total syhthesis of taxol. *Nature* 367, 630–634 (1994).

Nomoto et al., "Cloning and characterization of the alternative promoter regions of the human LIMK2 gene responsible for alternative transcripts with tissue-specific expression," *Gene,* 236(2):259–271, 1999.

Pasqualini and Ruoslahti, "Organ targeting in vivo using phage display peptide libraries," *Nature,* 380:364–366, 1996.

Pasqualini et al., "Aminopeptidase N is a receptor for tumor-homing peptides and a target for inhibiting angiogenesis," 2000 Feb.1;60(3):722–727, 2000.

Pasqualini, R. et al., Aminopeptidase N is a receptor for tumor-homing peptides and a target for inhibiting angiogenesis. *Cancer Res.* 60: 722–727 (2000).

Pietersz and McKenzie, "Antibody conjugates for the treatment of cancer," *Immunol. Rev.,* 129:57–80, 1992.

Ryser, H. J., Mandel, R., Hacobian, A. and Shen, W. C. Methotrexate-poly(lysine) as a selective agent for mutants of Chinese hamster ovary cells defective in endocytosis. *J. Cell. Physiol.* 135, 277–284 (1988).

Sambrook et al., In: *Molecular Cloning. A Laboratory Manual,* Vol. 1, Cold Spring Harbor Laboratory Press, Cold Spring Harbor, N.Y., Ch. 7,7.19–17.29, 1989.

Schultz and Mantsch, "Biochemical imaging and 2D classification of keratin pearl structures in oral squamous cell carcinoma," *Cell. Molec. Biol.,* 44(1):203–10, 1998.

Shin, Glisson, Khuri, Ginsberg, Papadimitrakopoulou, Lee, Lawhom, Gillenwater, Ang, Clayman, Callender, Hong, Lippman, "Phase II trial of paclitaxel, ifosfamide, and cisplatin in patients with recurrent head and neck squamous cell carcinoma," *J. Clinical Oncology,* 16(4):1325–30, 1998.

Shockley, Lin, Nagy, Tompkins, Dvorak, Yarmush, "Penetration of tumor tissue by antibodies and other immunoproteins," *Annals N. Y. Acad. Sci.,* 618:367–82, 1991.

Smith and Rutledge, "Chemotherapy in advanced ovarian cancer," *Natl. Cancer Inst. Monogr.,* 42:141–143, 1975.

Stewart and Young, Solid Phase Peptide Synthesis, 2d. ed., Pierce Chemical Co., 1984.

Tam et al., *J. Am. Chem. Soc.,* 105:6442, 1983.

Tsumaki et al., "Modular arrangement of cartilage- and neural tissue-specific cis-elements in the mouse alpha2 (XI) collagen promoter," *J Biol Chem.* 273(36):22861–22864, 1998.

U.S. Pat. No. 4,683,202
U.S. Pat. No. 5,925,565
U.S. Pat. No. 5,928,906
U.S. Pat. No. 5,935,819

Wada, "Adjuvant treatment of early stage non-small-cell lung cancer," *Oncology,* 13(7 Suppl 3):102–5, 1999.

Wu et al., "Promoter-dependent tissue-specific expressive nature of imprinting gene, insulin-like growth factor II, in human tissues," *Biochem Biophys Res Commun.* 233(1):221–226, 1997.

Wu et al., "Receptor-mediated in vitro gene transformation by a soluble DNA carrier system" *J. Biol. Chem.* 262, 4429–4432 (1987).

Young et al., *N. Engl. J. Med.,* 299:1261–1266, 1978.

Zhao-Emonet et al., "The equine herpes virus 4 thymidine kinase is a better suicide gene than the human herpes virus 1 thymidine kinase," *Gene Ther.* 6(9):1638–1642, 1999.

What is claimed is:

1. An isolated peptide that targets a tumor cell, wherein said peptide comprises the amino acid sequence of SEQ ID NO:1.

2. The peptide of claim 1, consisting of SEQ ID NO:1.

3. A composition comprising:
   a) an anti-cancer drug; and
   b) a peptide that targets a tumor cell, wherein said peptide comprises the amino acid sequence of SEQ ID NO:1.

4. The composition of claim 3, wherein said peptide consists of SEQ ID NO:1.

5. The composition of claim 3, wherein said drug is a chemotherapeutic agent.

6. The composition of claim 3, wherein said drug is a cytotoxic agent.

7. The composition of claim 3, wherein said drug is an apoptotic agent.

8. The composition of claim 3, wherein said drug is a DNA-damaging agent.

9. The composition of claim 3, wherein said drug is plant alkaloid.

10. The composition of claim 3, wherein said drug is cisplatin (CDDP), carboplatin, procarbazine, mechlorethamine, cyclophosphamide, ifosfamide, melphalan, chiorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin or methotrexate.

11. The peptide of claim 1, wherein said peptide is internalized by said tumor cell.

12. The composition of claim 3, wherein said peptide is internalized by said tumor cell.

13. The composition of claim 9, wherein said plant alkaloid is paclitaxel.

* * * * *